(12) United States Patent
Donders et al.

(10) Patent No.: US 8,140,167 B2
(45) Date of Patent: Mar. 20, 2012

(54) IMPLANTABLE THERAPY SYSTEM WITH EXTERNAL COMPONENT HAVING MULTIPLE OPERATING MODES

(75) Inventors: Adrianus Donders, Andover, MN (US); Mark Raymond Stultz, Maple Grove, MN (US); Koen Jacob Weijand, Alicante (ES)

(73) Assignee: EnteroMedics, Inc., St. Paul, MN (US)

( * ) Notice: Subject to any disclaimer, the term of this patent is extended or adjusted under 35 U.S.C. 154(b) by 996 days.

(21) Appl. No.: 11/943,069

(22) Filed: Nov. 20, 2007

(65) Prior Publication Data

US 2008/0300656 A1    Dec. 4, 2008

Related U.S. Application Data

(60) Provisional application No. 60/941,118, filed on May 31, 2007.

(51) Int. Cl.
*A61N 1/372* (2006.01)
(52) U.S. Cl. .............................. 607/60; 607/61
(58) Field of Classification Search ............... 607/60–61
See application file for complete search history.

(56) References Cited

U.S. PATENT DOCUMENTS

| | | | |
|---|---|---|---|
| 3,727,616 A | 4/1973 | Lenzkes | |
| 3,796,221 A | 3/1974 | Hagfors | |
| 3,942,535 A | 3/1976 | Schulman | |
| 4,082,097 A | 4/1978 | Mann et al. | |
| 4,369,530 A | 1/1983 | Robinson et al. | |
| 4,498,478 A | 2/1985 | Bourgeois | |
| 4,577,633 A | 3/1986 | Berkovits et al. | |
| 4,592,359 A | 6/1986 | Galbraith | |
| 4,608,985 A | 9/1986 | Crish et al. | |
| 4,612,934 A | 9/1986 | Borkan | |
| 4,793,353 A | 12/1988 | Borkan | |
| 4,846,180 A | 7/1989 | Buffet | |
| 4,979,511 A | 12/1990 | Terry, Jr. | |
| 5,215,089 A | 6/1993 | Baker, Jr. | |
| 5,251,634 A | 10/1993 | Weinberg | |
| 5,263,480 A | 11/1993 | Wernicke et al. | |
| 5,279,292 A | 1/1994 | Baumann et al. | |

(Continued)

FOREIGN PATENT DOCUMENTS

EP    1 666 087 A2    6/2006

(Continued)

OTHER PUBLICATIONS

Kilgore, K. et al., "Nerve Conduction Block Utilising High-Frequency Alternating Current," *Medical & Biological Engineering & Computing*, vol. 42, pp. 394-406 (2004).

(Continued)

*Primary Examiner* — Carl H Layno
*Assistant Examiner* — Paula J Stice
(74) *Attorney, Agent, or Firm* — Merchant & Gould P.C.

(57) ABSTRACT

A therapy system for applying an electrical signal to an internal anatomical feature of a patient includes an implantable component and an external component. The external component can be configured into one of multiple selectable operating modes. The therapy system also may include a first external antenna configured to communicate with the implantable component and a second external antenna configured to communicate with the implantable component. Plugging one of the external antennas into the external component automatically configures the external component into one of the operating modes.

16 Claims, 15 Drawing Sheets

U.S. PATENT DOCUMENTS

| | | | |
|---|---|---|---|
| 5,360,437 | A | 11/1994 | Thompson |
| 5,391,188 | A | 2/1995 | Nelson et al. |
| 5,531,778 | A | 7/1996 | Maschino et al. |
| 5,591,217 | A * | 1/1997 | Barreras .................. 607/61 |
| 5,716,377 | A | 2/1998 | Rise et al. |
| 5,733,313 | A | 3/1998 | Barreras, Sr. et al. |
| 5,749,907 | A | 5/1998 | Mann |
| 5,755,747 | A | 5/1998 | Daly et al. |
| 5,836,989 | A | 11/1998 | Shelton |
| 5,876,425 | A | 3/1999 | Gord et al. |
| 5,928,272 | A | 7/1999 | Adkins et al. |
| 6,045,513 | A | 4/2000 | Stone et al. |
| 6,067,474 | A | 5/2000 | Schulman et al. |
| 6,102,874 | A | 8/2000 | Stone et al. |
| 6,167,311 | A | 12/2000 | Rezai |
| 6,205,358 | B1 | 3/2001 | Haeg et al. |
| 6,208,902 | B1 | 3/2001 | Boveja |
| 6,243,606 | B1 | 6/2001 | Mann et al. |
| 6,278,258 | B1 | 8/2001 | Echarri et al. |
| 6,280,409 | B1 | 8/2001 | Stone et al. |
| 6,285,908 | B1 | 9/2001 | Mann et al. |
| 6,305,381 | B1 | 10/2001 | Weijand et al. |
| 6,321,117 | B1 | 11/2001 | Koshiol et al. |
| 6,356,786 | B1 | 3/2002 | Rezai et al. |
| 6,363,282 | B1 | 3/2002 | Nichols et al. |
| 6,366,814 | B1 | 4/2002 | Boveja et al. |
| 6,381,496 | B1 | 4/2002 | Meadows et al. |
| 6,418,346 | B1 | 7/2002 | Nelson et al. |
| 6,438,423 | B1 | 8/2002 | Rezai et al. |
| 6,473,652 | B1 | 10/2002 | Sarwal et al. |
| 6,505,074 | B2 | 1/2003 | Boveja et al. |
| 6,505,075 | B1 | 1/2003 | Weiner |
| 6,505,077 | B1 | 1/2003 | Kast et al. |
| 6,516,227 | B1 | 2/2003 | Meadows et al. |
| 6,564,102 | B1 | 5/2003 | Boveja |
| 6,587,719 | B1 | 7/2003 | Barrett et al. |
| 6,600,956 | B2 | 7/2003 | Maschino et al. |
| 6,609,025 | B2 | 8/2003 | Barrett et al. |
| 6,611,715 | B1 | 8/2003 | Boveja |
| 6,614,406 | B2 | 9/2003 | Amundson et al. |
| 6,615,081 | B1 | 9/2003 | Boveja |
| 6,662,052 | B1 | 12/2003 | Sarwal et al. |
| 6,664,763 | B2 | 12/2003 | Echarri et al. |
| 6,678,560 | B1 * | 1/2004 | Gilkerson et al. .............. 607/14 |
| 6,690,974 | B2 | 2/2004 | Archer et al. |
| 6,760,626 | B1 | 7/2004 | Boveja |
| 6,819,956 | B2 | 11/2004 | DiLorenzo |
| 6,850,803 | B1 | 2/2005 | Jimenez et al. |
| 6,879,859 | B1 | 4/2005 | Boveja |
| 6,892,097 | B2 | 5/2005 | Holsheimer |
| 6,895,280 | B2 | 5/2005 | Meadows et al. |
| 6,907,295 | B2 | 6/2005 | Gross et al. |
| 6,934,580 | B1 | 8/2005 | Osorio et al. |
| 6,985,773 | B2 | 1/2006 | Von Arx et al. |
| 7,003,353 | B1 | 2/2006 | Parkhouse |
| 7,076,307 | B2 | 7/2006 | Boveja et al. |
| 7,082,333 | B1 | 7/2006 | Bauhahn et al. |
| 7,146,223 | B1 | 12/2006 | King |
| 7,167,750 | B2 | 1/2007 | Knudson et al. |
| 7,191,012 | B2 | 3/2007 | Boveja et al. |
| 7,239,918 | B2 | 7/2007 | Strother et al. |
| 7,283,867 | B2 | 10/2007 | Strother et al. |
| 7,286,881 | B2 | 10/2007 | Schommer et al. |
| 7,486,993 | B2 | 2/2009 | Gilmer et al. |
| 7,551,960 | B2 | 6/2009 | Forsberg et al. |
| 7,715,913 | B1 | 5/2010 | Froman et al. |
| 7,725,195 | B2 * | 5/2010 | Lima et al. ...................... 607/60 |
| 7,801,615 | B2 | 9/2010 | Meadows et al. |
| 7,813,809 | B2 | 10/2010 | Strother et al. |
| 2001/0051787 | A1 | 12/2001 | Haller et al. |
| 2002/0013614 | A1 | 1/2002 | Thompson |
| 2002/0021244 | A1 * | 2/2002 | Aizawa et al. ........... 342/357.12 |
| 2003/0171789 | A1 | 9/2003 | Malek et al. |
| 2003/0172940 | A1 | 9/2003 | Rogers et al. |
| 2003/0212440 | A1 | 11/2003 | Boveja |
| 2004/0122487 | A1 | 6/2004 | Hatlestad et al. |
| 2004/0215089 | A1 | 10/2004 | Bergelson et al. |
| 2004/0249416 | A1 | 12/2004 | Yun et al. |
| 2004/0267333 | A1 | 12/2004 | Kronberg |
| 2005/0004628 | A1 | 1/2005 | Goetz et al. |
| 2005/0021092 | A1 | 1/2005 | Yun et al. |
| 2005/0038484 | A1 | 2/2005 | Knudson et al. |
| 2005/0049655 | A1 | 3/2005 | Boveja et al. |
| 2005/0065573 | A1 | 3/2005 | Rezai |
| 2005/0070968 | A1 | 3/2005 | Bergelson et al. |
| 2005/0075684 | A1 * | 4/2005 | Phillips et al. .................. 607/60 |
| 2005/0075693 | A1 | 4/2005 | Toy et al. |
| 2005/0107841 | A1 | 5/2005 | Meadows et al. |
| 2005/0113889 | A1 | 5/2005 | Jimenez et al. |
| 2005/0131467 | A1 | 6/2005 | Boveja |
| 2005/0131484 | A1 | 6/2005 | Boveja et al. |
| 2005/0131485 | A1 | 6/2005 | Knudson et al. |
| 2005/0131486 | A1 | 6/2005 | Boveja et al. |
| 2005/0131487 | A1 | 6/2005 | Boveja et al. |
| 2005/0131493 | A1 | 6/2005 | Boveja et al. |
| 2005/0137644 | A1 | 6/2005 | Boveja et al. |
| 2005/0143783 | A1 | 6/2005 | Boveja et al. |
| 2005/0143786 | A1 | 6/2005 | Boveja |
| 2005/0143787 | A1 | 6/2005 | Boveja et al. |
| 2005/0143788 | A1 | 6/2005 | Yun et al. |
| 2005/0149146 | A1 | 7/2005 | Boveja et al. |
| 2005/0187590 | A1 | 8/2005 | Boveja et al. |
| 2005/0192644 | A1 | 9/2005 | Boveja et al. |
| 2005/0197678 | A1 | 9/2005 | Boveja et al. |
| 2005/0209654 | A1 | 9/2005 | Boveja et al. |
| 2005/0228693 | A1 | 10/2005 | Webb et al. |
| 2005/0288736 | A1 | 12/2005 | Persen et al. |
| 2006/0030891 | A1 | 2/2006 | Saltzstein et al. |
| 2006/0052836 | A1 | 3/2006 | Kim et al. |
| 2006/0074450 | A1 | 4/2006 | Boveja et al. |
| 2006/0085040 | A1 | 4/2006 | VanDanacker |
| 2006/0195152 | A1 | 8/2006 | Gerber |
| 2006/0247711 | A1 | 11/2006 | Verhoef et al. |
| 2007/0043411 | A1 | 2/2007 | Foster et al. |
| 2007/0060916 | A1 | 3/2007 | Pappone |
| 2007/0067000 | A1 | 3/2007 | Strother et al. |
| 2007/0067004 | A1 | 3/2007 | Boveja et al. |
| 2007/0106346 | A1 | 5/2007 | Bergelson et al. |
| 2007/0191912 | A1 | 8/2007 | Fischer et al. |
| 2007/0250121 | A1 | 10/2007 | Miesel et al. |
| 2007/0270921 | A1 | 11/2007 | Strother et al. |
| 2008/0015641 | A1 | 1/2008 | Armstrong et al. |
| 2008/0097554 | A1 | 4/2008 | Payne et al. |
| 2008/0132974 | A1 | 6/2008 | Strother et al. |
| 2008/0221644 | A1 | 9/2008 | Vallapureddy et al. |
| 2008/0300654 | A1 | 12/2008 | Lambert et al. |
| 2008/0300657 | A1 | 12/2008 | Stultz |
| 2008/0303480 | A1 | 12/2008 | Prutchi et al. |
| 2009/0112291 | A1 | 4/2009 | Wahlstrand et al. |
| 2009/0259273 | A1 | 10/2009 | Figueiredo et al. |
| 2009/0264966 | A1 | 10/2009 | Blum et al. |
| 2010/0256709 | A1 | 10/2010 | Kallmyer |
| 2010/0256710 | A1 | 10/2010 | Dinsmoor et al. |
| 2010/0268305 | A1 | 10/2010 | Olson et al. |
| 2011/0004269 | A1 | 1/2011 | Strother et al. |
| 2011/0004278 | A1 | 1/2011 | Aghassian et al. |

FOREIGN PATENT DOCUMENTS

WO      WO 01/43821 A1      6/2001

OTHER PUBLICATIONS

Product Brochure, "ATROSTIM Phrenic Nerve Stimulator," AtroTech Oy, P.O. Box 28, Fin-33721,Tampere, Finland, 2 pages (Jun. 2004).

Solomonow, M. et al., "Control of Muscle Contractile Force Through Indirect High-Frequency Stimulation," *American Journal of Physical Medicine*, vol. 62, No. 2, pp. 71-82 (1983).

Invitation to Pay Additional Fees with Partial International Search mailed Aug. 28, 2008.

Invitation to Pay Additional Fees with Partial International Search cited in PCT/US2008/055098 mailed Jul. 11, 2008.

U.S. Non-Final Office Action mailed Dec. 8, 2010 in Lambert et al., U.S. Appl. No. 11/943,054, filed Nov. 20, 2007, and titled "Implantable Therapy System."

U.S. Non-Final Office Action mailed Sep. 24, 2010 in Vallapureddy et al., U.S. Appl. No. 11/716,353, filed Mar. 9, 2007, and titled "Remote Monitoring and Control of Implantable Devices."

U.S. Final Office Action mailed Feb. 1, 2011 in Vallapureddy et al., U.S. Appl. No. 11/716,353, filed Mar. 9, 2007, and titled "Remote Monitoring and Control of Implantable Devices."

U.S. Final Office Action cited in U.S. Appl. No. 11/943,054 mailed Apr. 6, 2011.

U.S. Non-Final Office Action cited in U.S. Appl. No. 11/943,093 mailed Jul. 7, 2011.

* cited by examiner

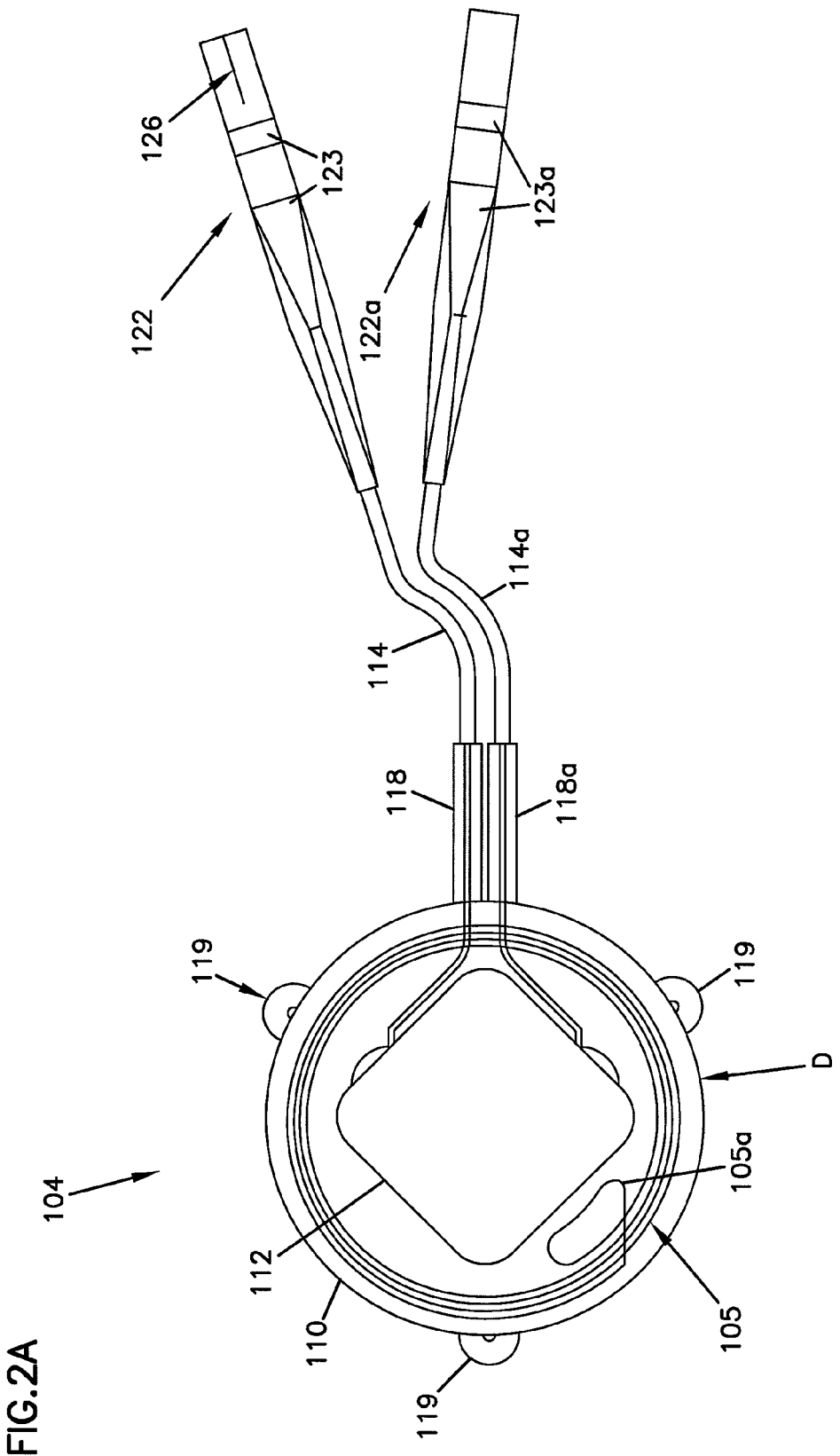

IMPLANTABLE THERAPY SYSTEM WITH EXTERNAL COMPONENT HAVING MULTIPLE OPERATING MODES

CROSS REFERENCE

This application claims priority to U.S. Provisional Application Ser. No. 60/941,118, filed May 31, 2007, and entitled "IMPLANTABLE DEVICE," the disclosure of which is hereby incorporated by reference herein.

This application discloses and claims subject matter disclosed in commonly assigned U.S. application Ser. Nos. 11/943,093 and 11/943,054, filed concurrently herewith and titled "Therapy System" and "Implantable Therapy System," respectively.

I. BACKGROUND OF THE INVENTION

1. Field of the Invention

This invention pertains to systems for applying electrical signals to an anatomical feature of a patient. While many of the disclosed concepts are applicable to a wide variety of therapies (e.g., cardiac pacing with electrodes applied to heart tissue), the invention is described in a preferred embodiment where the invention pertains to the treatment of gastro-intestinal disorders such as obesity, pancreatitis, irritable bowel syndrome and inflammatory disorders. In a most preferred embodiment, this invention pertains to the treatment of a gastrointestinal disorder by the application of a high frequency signal to a vagus nerve of a patient.

2. Description of the Prior Art

A blocking therapy can be used alone or in combination with traditional electrical nerve stimulation in which impulses are created for propagation along a nerve. The disorders to be treated include, without limitation, functional gastrointestinal disorders (FGIDs) (such as functional dyspepsia (dysmotility-like) and irritable bowel syndrome (IBS)), gastroparesis, gastroesophageal reflux disease (GERD), inflammation, discomfort and other disorders.

In a blocking therapy, an electrode (or multiple electrodes) is placed on or near a vagus nerve or nerves of a patient. By "near", it is meant close enough that a field created by the electrode captures the nerve. As disclosed in the foregoing patent and applications, the electrode can be placed directly on a nerve, overlying tissue surrounding a nerve or on or in an organ near a nerve.

Higher frequencies (e.g., 2,500 Hz-20,000 Hz) are believed to result in more consistent neural conduction block. Particularly, the nerve conduction block is applied with an electrical signal selected to block the entire cross-section of the nerve (e.g., both afferent and efferent signals on both myelinated and non-myelinated fibers) at the site of application of the blocking signal.

In one embodiment of the electrodes a signal amplitude of 0.5 mA to 8 mA at the electrode-nerve interface has been found to be adequate for blocking. However, depending on electrode design, other amplitudes may suffice. Other signal parameters, as non-limiting examples, include an adjustable pulse width (e.g., 50 μsec to 500 μsec), and a frequency range of (by non-limiting example) 1000 Hz to 10,000 Hz. It must be recognized that the frequency sets certain limitations on the available pulse width; for example, the pulse width cannot exceed 50% of the cycle time for a symmetrical biphasic pulse.

A typical duty cycle of therapy could consist of 5 minutes on and 10 minutes off. These are representative only. For example, a duty cycle could be 2 minutes on and 5 minutes off or be 30 minutes on per day. These examples are given to illustrate the wide latitude available in selecting particular signal parameters for a particular patient.

A complete system for applying a signal to a nerve may include systems for addressing the potential for charge build-up, assuring good communication between implanted and external components, recharging implantable batteries, physician and patient controls and programming and communication with the system. These issues and selected prior art systems for addressing these issues will now be discussed.

II. SUMMARY OF THE INVENTION

According to a preferred embodiment of the present invention, a therapy system is disclosed for applying therapy to an internal anatomical feature of a patient. The system includes at least one electrode for implantation within the patient and placement at the anatomical feature (e.g., a nerve) for applying the therapy signal to the feature upon application of a treatment signal to the electrode. An implantable component is placed in the patient's body beneath a skin layer and coupled to the electrode. The implantable component includes an implanted antenna. An external component has an external antenna for placement above the skin and adapted to be electrically coupled to the implanted antenna across the skin through radiofrequency transmission.

According to aspects, the external component is adapted to be configured into multiple selectable operating modes including an operating room mode, a programming mode, and a charging mode.

For example, communicatively coupling the external component to peripheral devices can automatically configure the external component into one of the operating modes.

According to other aspects, the implantable component is adapted to be configured into multiple selectable operating modes including a training mode for simulating a therapy, and a therapy mode for providing therapy.

According to other aspects, the implantable component may be configured to increment therapy settings automatically by a predetermined amount after a predetermined period of time.

III. BRIEF DESCRIPTION OF THE DRAWINGS

FIG. 2A is a plan view of an implantable neuroregulator for use in the therapy system of FIG. 1 according to aspects of the present disclosure;

IV. DETAILED DESCRIPTION OF THE PREFERRED EMBODIMENT

With reference now to the various drawing figures in which identical elements are numbered identically throughout, a description of the preferred embodiments of the present invention will now be described. While the invention is applicable to treating a wide variety of gastro-intestinal disorders, the invention will be described in preferred embodiments for the treatment of obesity.

Figure 1:
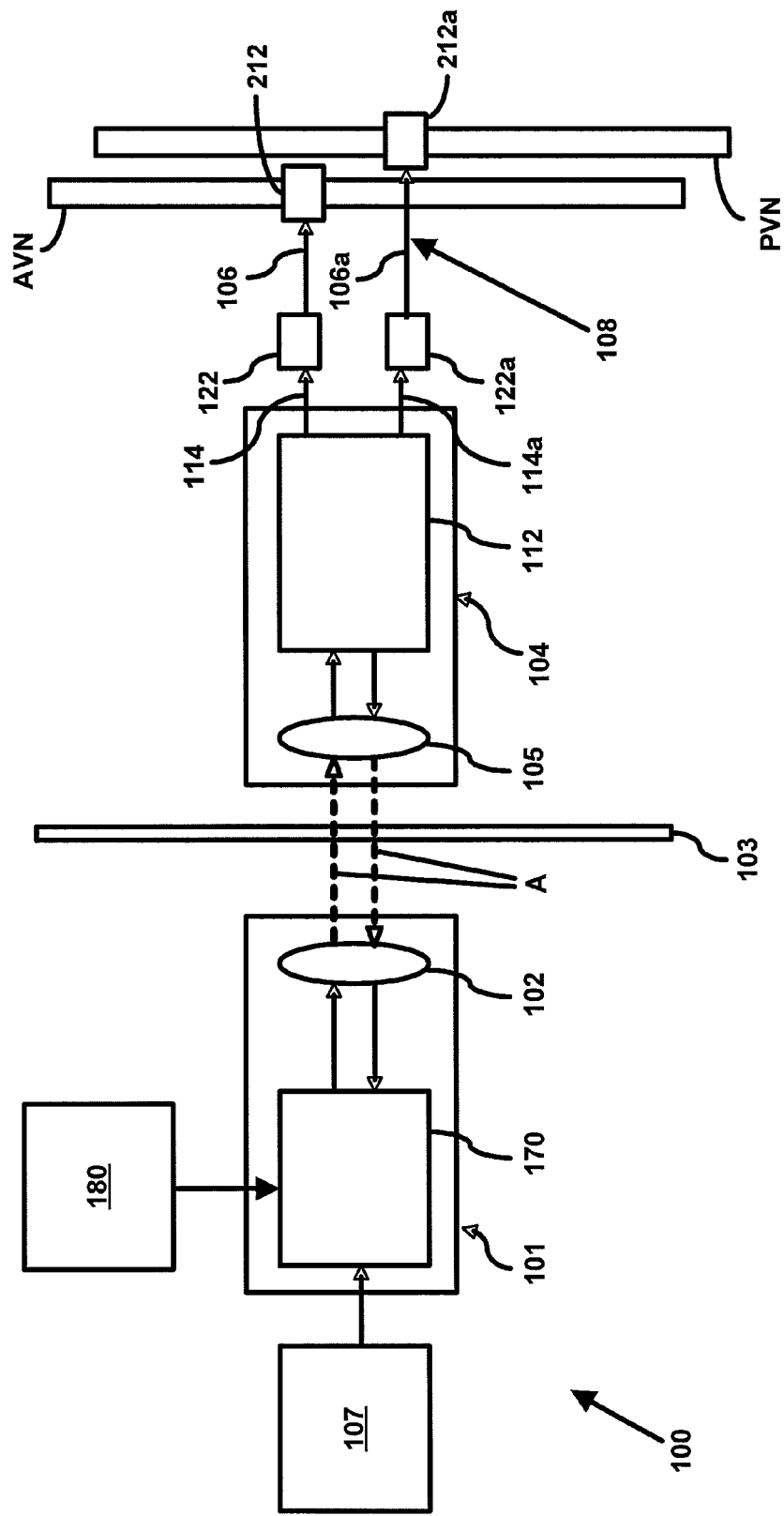
FIG. 1 is a schematic representation of a therapy system having features that are examples of inventive aspects of the principles of the present invention, the therapy system including a neuroregulator and an external charger.

FIG. 1 schematically illustrates a therapy system 100 for treating obesity or other gastro-intestinal disorders. The therapy system 100 includes a neuroregulator 104, an electrical lead arrangement 108, and an external charger 101. The neuroregulator 104 is adapted for implantation within a patient to be treated for obesity. As will be more fully described herein, the neuroregulator 104 typically is implanted just beneath a skin layer 103.

The neuroregulator 104 is configured to connect electrically to the lead arrangement 108. In general, the lead arrangement 108 includes two or more electrical lead assemblies 106, 106a. In the example shown, the lead arrangement 108 includes two identical (bipolar) electrical lead assemblies 106, 106a. The neuroregulator 104 generates therapy signals and transmits the therapy signals to the lead assemblies 106, 106a.

The lead assemblies 106, 106a up-regulate and/or down-regulate nerves of a patient based on the therapy signals provided by the neuroregulator 104. In an embodiment, the lead assemblies 106, 106a include distal electrodes 212, 212a, which are placed on one or more nerves of a patient. For example, the electrodes 212, 212a may be individually placed on the anterior vagal nerve AVN and posterior vagal nerve PVN, respectively, of a patient. For example, the distal electrodes 212, 212a can be placed just below the patient's diaphragm. In other embodiments, however, fewer or more electrodes can be placed on or near fewer or more nerves.

The external charger 101 includes circuitry for communicating with the implanted neuroregulator 104. In general, the communication is transmitted across the skin 103 along a two-way signal path as indicated by arrows A. Example communication signals transmitted between the external charger 101 and the neuroregulator 104 include treatment instructions, patient data, and other signals as will be described herein. Energy also can be transmitted from the external charger 101 to the neuroregulator 104 as will be described herein.

In the example shown, the external charger 101 can communicate with the implanted neuroregulator 104 via bidirectional telemetry (e.g. via radiofrequency (RF) signals). The external charger 101 shown in FIG. 1 includes a coil 102, which can send and receive RF signals. A similar coil 105 can be implanted within the patient and coupled to the neuroregulator 104. In an embodiment, the coil 105 is integral with the neuroregulator 104. The coil 105 serves to receive and transmit signals from and to the coil 102 of the external charger 101.

For example, the external charger 101 can encode the information as a bit stream by amplitude modulating or frequency modulating an RF carrier wave. The signals transmitted between the coils 102, 105 preferably have a carrier frequency of about 6.78 MHz. For example, during an information communication phase, the value of a parameter can be transmitted by toggling a rectification level between half-wave rectification and no rectification. In other embodiments, however, higher or lower carrier wave frequencies may be used.

In an embodiment, the neuroregulator 104 communicates with the external charger 101 using load shifting (e.g., modification of the load induced on the external charger 101). This change in the load can be sensed by the inductively coupled external charger 101. In other embodiments, however, the neuroregulator 104 and external charger 101 can communicate using other types of signals.

In an embodiment, the neuroregulator 104 receives power to generate the therapy signals from an implantable power source 151 (see FIG. 3A), such as a battery. In a preferred embodiment, the power source 151 is a rechargeable battery. In some embodiments, the power source 151 can provide power to the implanted neuroregulator 104 when the external charger 101 is not connected. In other embodiments, the external charger 101 also can be configured to provide for periodic recharging of the internal power source 151 of the neuroregulator 104. In an alternative embodiment, however, the neuroregulator 104 can entirely depend upon power received from an external source (see FIG. 3B). For example, the external charger 101 can transmit power to the neuroregulator 104 via the RF link (e.g., between coils 102, 105).

In some embodiments, the neuroregulator 104 initiates the generation and transmission of therapy signals to the lead assemblies 106, 106a. In an embodiment, the neuroregulator 104 initiates therapy when powered by the internal battery 151. In other embodiments, however, the external charger 101 triggers the neuroregulator 104 to begin generating therapy signals. After receiving initiation signals from the external charger 101, the neuroregulator 104 generates the therapy signals (e.g., pacing signals) and transmits the therapy signals to the lead assemblies 106, 106a.

In other embodiments, the external charger 101 also can provide the instructions according to which the therapy signals are generated (e.g., pulse-width, amplitude, and other such parameters). In a preferred embodiment, the external charger 101 includes memory in which several predetermined programs/therapy schedules can be stored for transmission to the neuroregulator 104. The external charger 101 also can enable a user to select a program/therapy schedule stored in memory for transmission to the neuroregulator 104. In another embodiment, the external charger 101 can provide treatment instructions with each initiation signal.

Typically, each of the programs/therapy schedules stored on the external charger 101 can be adjusted by a physician to suit the individual needs of the patient. For example, a computing device (e.g., a notebook computer, a personal computer, etc.) 107 can be communicatively connected to the external charger 101. With such a connection established, a physician can use the computing device 107 to program therapies into the external charger 101 for either storage or transmission to the neuroregulator 104.

The neuroregulator 104 also may include memory 152 (see FIGS. 3A and 3B) in which treatment instructions and/or patient data can be stored. For example, the neuroregulator 104 can store therapy programs indicating what therapy should be delivered to the patient. The neuroregulator 104 also can store patient data indicating how the patient utilized the therapy system 100 and/or reacted to the delivered therapy.

Figure 3A:
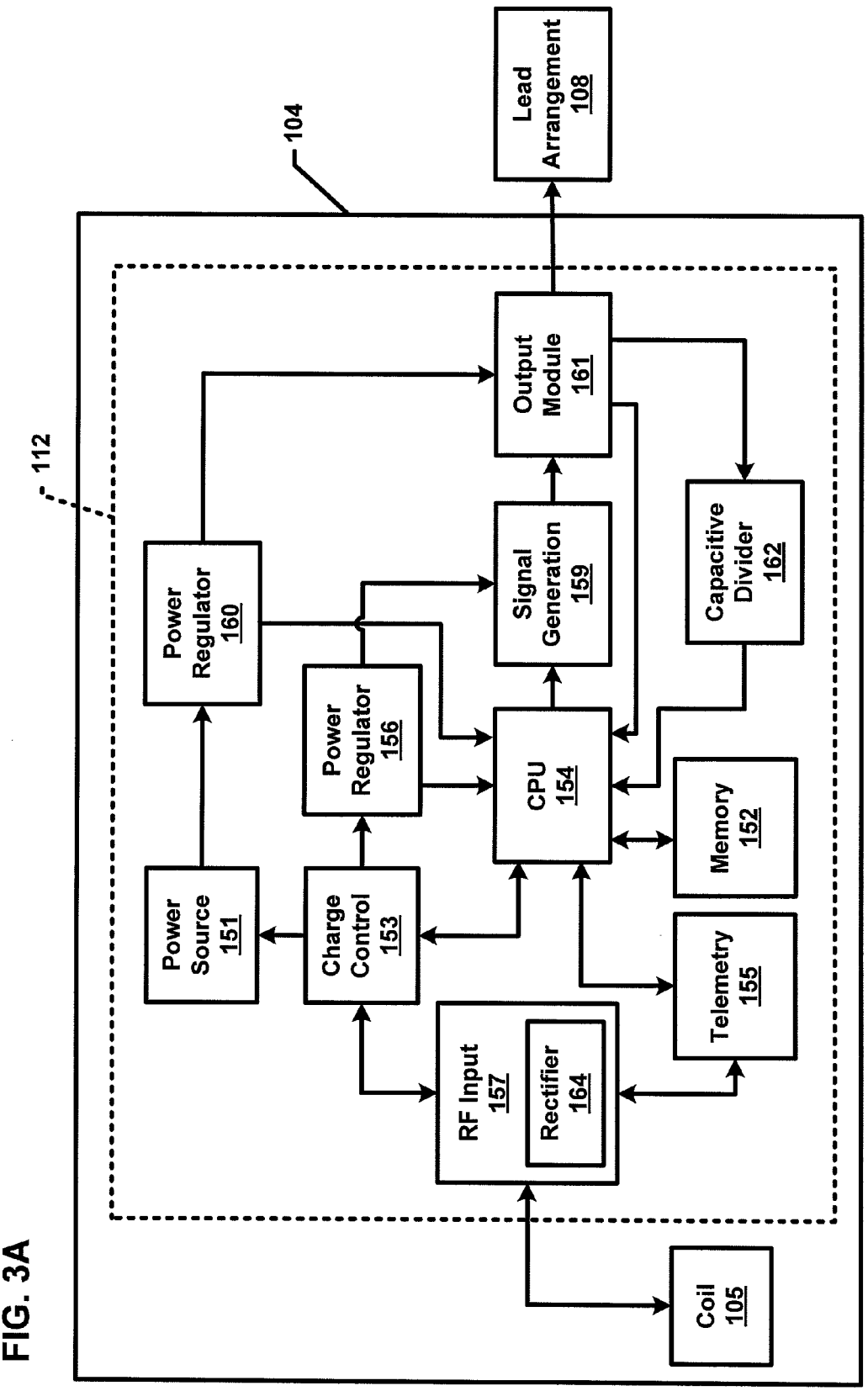
FIG. 3A is a block diagram of a representative circuit module for the neuroregulator of FIG. 2A and FIG. 2B according to aspects of the present disclosure.

In what follows, the focus of the detailed description is the preferred embodiment in which the neuroregulator 104 contains a rechargeable battery 151 from which the neuroregulator 104 may draw power (FIG. 3A).

1. System Hardware Components a. Neuroregulator

Figure 2B:
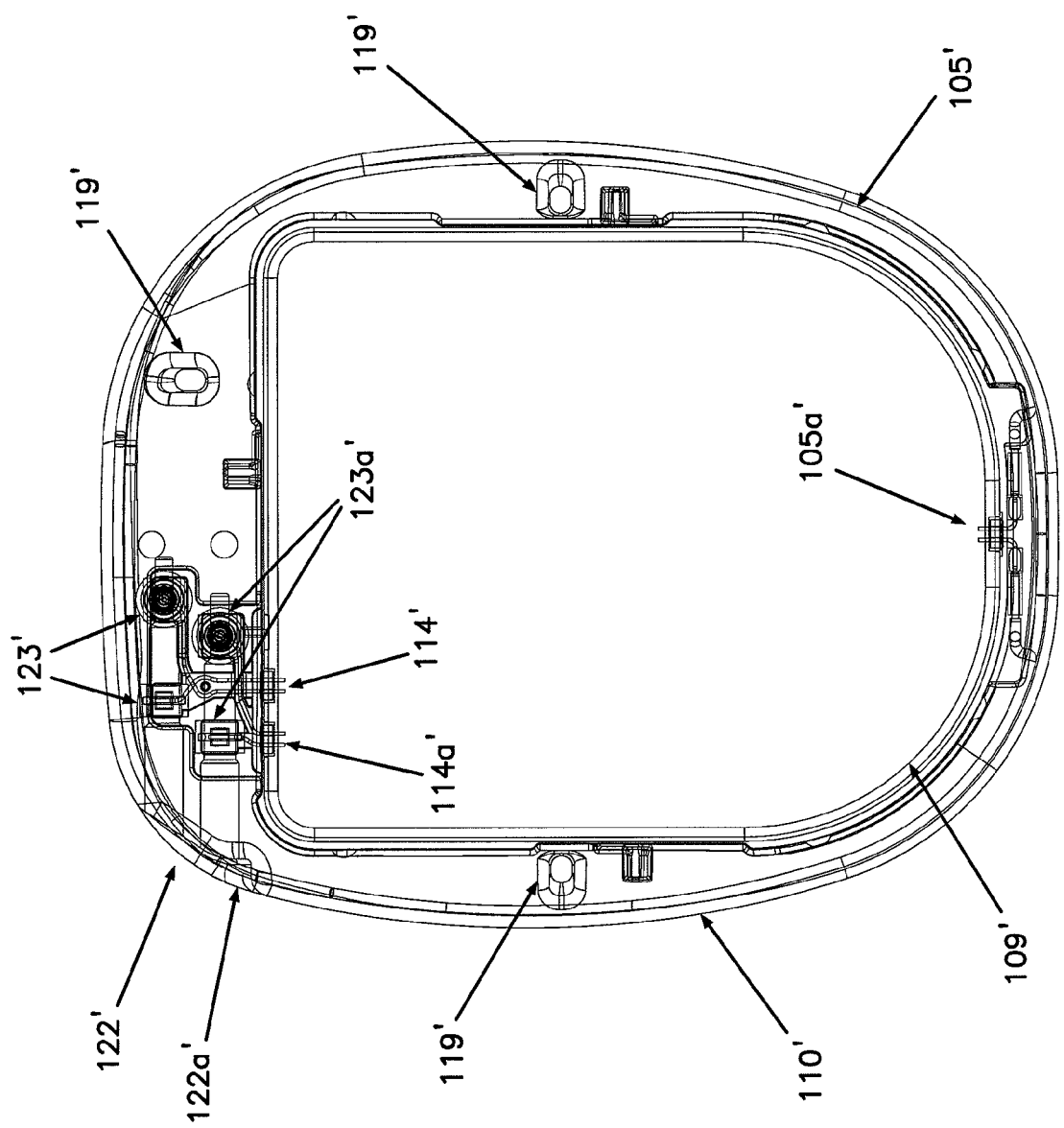
FIG. 2B is a plan view of another implantable neuroregulator for use in the therapy system of FIG. 1 according to aspects of the present disclosure.

Different embodiments of the neuroregulator 104, 104' are illustrated schematically in FIGS. 2A and 2B, respectively. The neuroregulator 104, 104' is configured to be implanted subcutaneously within the body of a patient. Preferably, the neuroregulator 104, 104' is implanted subcutaneously on the thoracic sidewall in the area slightly anterior to the axial line and caudal to the arm pit. In other embodiments, alternative implantation locations may be determined by the implanting surgeon.

The neuroregulator 104, 104' is generally sized for such implantation in the human body. By way of non-limiting example, an outer diameter D, D' of the neuroregulator 104, 104' is typically less than or equal to about sixty mm and a thickness of the neuroregulator 104, 104' is less than or equal to about fifteen mm. In a preferred embodiment, the neuroregulator 104, 104' has a maximum outer diameter D, D' of about fifty-five mm and a maximum thickness of about nine mm. In one embodiment, the neuroregulator 104, 104' weighs less than about one hundred twenty grams.

Typically, the neuroregulator 104, 104' is implanted parallel to the skin surface to maximize RF coupling efficiency with the external charger 101. In an embodiment, to facilitate optimal information and power transfer between the internal coil 105, 105' of the neuroregulator 104, 104' and the external coil 102 of the external charger 101, the patient can ascertain the position of the neuroregulator 104, 104' (e.g., through palpation or with the help of a fixed marking on the skin). In an embodiment, the external charger 101 can facilitate coil positioning as discussed herein with reference to FIGS. 7 and 8.

As shown in FIGS. 2A and 2B, the neuroregulator 104, 104' generally includes a housing 109, 109' overmolded with the internal coil 105, 105', respectively. The overmold 110, 110' of the neuroregulator 104, 104' is formed from a bio-compatible material that is transmissive to RF signals (i.e., or other such communication signals). Some such bio-compatible materials are well known in the art. For example, the overmold 110, 110' of the neuroregulator 104, 104' may be formed from silicone rubber or other suitable materials. The overmold 110, 110' also can include suture tabs or holes 119, 119' to facilitate placement within the patient's body.

The housing 109, 109' of the neuroregulator 104, 104' also may contain a circuit module, such as circuit 112 (see FIGS. 1, 3A, and 3B), to which the coil 105, 105' may be electrically connected along a path 105a, 105a'. The circuit module within the housing 109 may be electrically connected to the lead assemblies 106, 106a (FIG. 1) through conductors 114, 114a. In the example shown in FIG. 2A, the conductors 114, 114a extend out of the housing 109 through strain reliefs 118, 118a. Such conductors 114, 114a are well known in the art.

The conductors 114, 114a terminate at connectors 122, 122a, which are configured to receive or otherwise connect the lead assemblies 106, 106a (FIG. 1) to the conductors 114, 114a. By providing connectors 122, 122a between the neuroregulator 104 and the lead assemblies 106, 106a, the lead assemblies 106, 106a may be implanted separately from the neuroregulator 104. Also, following implantation, the lead assemblies 106, 106a may be left in place while the originally implanted neuroregulator 104 is replaced by a different neuroregulator.

As shown in FIG. 2A, the neuroregulator connectors 122, 122a can be configured to receive connectors 126 of the lead assemblies 106, 106a. For example, the connectors 122, 122a of the neuroregulator 104 may be configured to receive pin connectors (not shown) of the lead assemblies 106, 106a. In another embodiment, the connectors 122, 122a may be configured to secure to the lead assemblies 106, 106a using set-screws 123, 123a, respectively, or other such fasteners. In a preferred embodiment, the connectors 122, 122a are well-known IS-1 connectors. As used herein, the term "IS-1" refers to a connector standard used by the cardiac pacing industry, and is governed by the international standard ISO 5841-3.

In the example shown in FIG. 2B, female connectors 122', 122a' configured to receive the leads 106, 106a are molded into a portion of the overmold 110' of the neuroregulator 104'. The leads connectors 126 are inserted into these molded connectors 122', 122a' and secured via setscrews 123', 123a', seals (e.g., Bal Seals®), and/or another fastener.

The circuit module 112 (see FIGS. 1, 3A, and 3B) is generally configured to generate therapy signals and to transmit the therapy signals to the lead assemblies 106, 106a. The circuit module 112 also may be configured to receive power and/or data transmissions from the external charger 101 via the internal coil 105. The internal coil 105 may be configured to send the power received from the external charger to the circuit module 112 for use or to the internal power source (e.g., battery) 151 of the neuroregulator 104 to recharge the power source 151.

Figure 3B:
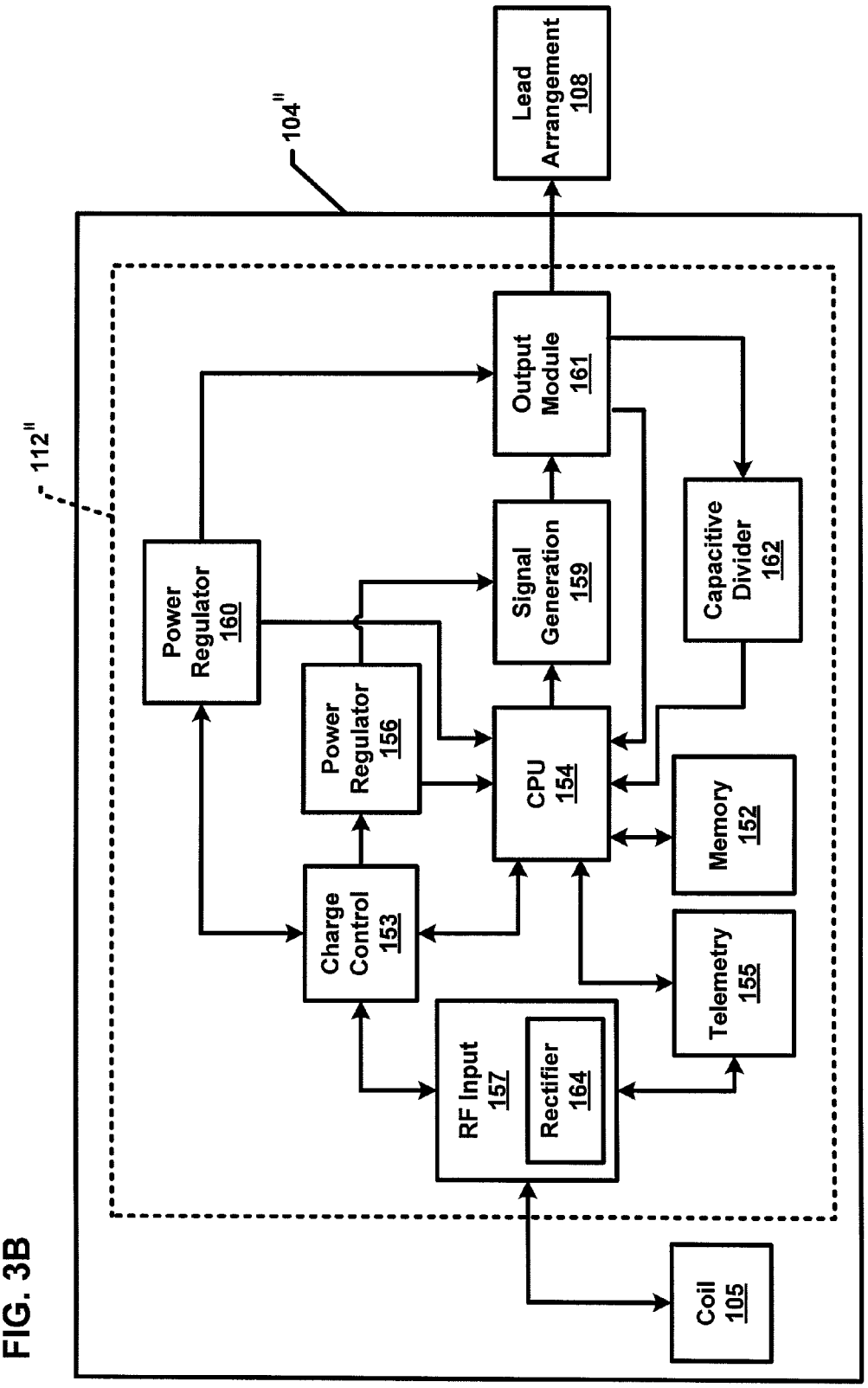
FIG. 3B is a block diagram of another representative circuit module for the neuroregulator of FIG. 2A and FIG. 2B according to aspects of the present disclosure.

Block diagrams of example circuit modules 112, 112" are shown in FIGS. 3A, 3B, respectively. Either circuit module 112, 112" can be utilized with any neuroregulator, such as neuroregulators 104, 104' described above. The circuit modules 112, 112" differ in that the circuit module 112 includes an internal power source 151 and a charge control module 153 and the circuit module 112" does not. Accordingly, power for operation of the circuit module 112" is provided entirely by the external charger 101 via the internal coil 105. Power operation for circuit module 112 may be provided by the external charger 101 or by the internal power source 151. Either circuit module 112, 112" may be used with either neuroregulator 104, 104' shown in FIGS. 2A, 2B. For ease in understanding, the following description will focus on the circuit module 112 shown in FIG. 3A.

The circuit module 112 includes an RF input 157 including a rectifier 164. The rectifier 164 converts the RF power received from the internal coil 105 into DC electric current. For example, the RF input 157 may receive the RF power from the internal coil 105, rectify the RF power to a DC power, and transmit the DC current to the internal power source 151 for storage. In one embodiment, the RF input 157 and the coil 105 may be tuned such that the natural frequency maximizes the power transferred from the external charger 101.

In an embodiment, the RF input 157 can first transmit the received power to a charge control module 153. The charge control module 153 receives power from the RF input 157 and delivers the power where needed through a power regulator 156. For example, the RF input 157 may forward the power to the battery 151 for charging or to circuitry for use in creating therapy signals as will be described below. When no power is received from the coil 105, the charge control 153 may draw power from the battery 151 and transmit the power through the power regulator 160 for use. For example, a central processing unit (CPU) 154 of the neuroregulator 104 may manage the charge control module 153 to determine whether power obtained from the coil 105 should be used to recharge the power source 151 or whether the power should be used to produce therapy signals. The CPU 154 also may determine when the power stored in the power source 151 should be used to produce therapy signals.

The transmission of energy and data via RF/inductive coupling is well known in the art. Further details describing recharging a battery via an RF/inductive coupling and controlling the proportion of energy obtained from the battery with energy obtained via inductive coupling can be found in the following references, all of which are hereby incorporated by reference herein: U.S. Pat. No. 3,727,616, issued Apr. 17, 1973, U.S. Pat. No. 4,612,934, issued Sep. 23, 1986, U.S. Pat. No. 4,793,353, issued Dec. 27, 1988, U.S. Pat. No. 5,279,292, issued Jan. 18, 1994, and U.S. Pat. No. 5,733,313, issued Mar. 31, 1998.

In general, the internal coil 105 may be configured to pass data transmissions between the external charger 101 and a telemetry module 155 of the neuroregulator 104. The telemetry module 155 generally converts the modulated signals received from the external charger 101 into data signals understandable to the CPU 154 of the neuroregulator 104. For example, the telemetry module 155 may demodulate an amplitude modulated carrier wave to obtain a data signal. In one embodiment, the signals received from the internal coil 105 are programming instructions from a physician (e.g., provided at the time of implant or on subsequent follow-up visits). The telemetry module 155 also may receive signals (e.g., patient data signals) from the CPU 154 and may send the data signals to the internal coil 105 for transmission to the external charger 101.

The CPU 154 may store operating parameters and data signals received at the neuroregulator 104 in an optional memory 152 of the neuroregulator 104. Typically, the memory 152 includes non-volatile memory. In other embodiments, the memory 152 also can store serial numbers and/or model numbers of the leads 106; serial number, model number, and/or firmware revision number of the external charger 101; and/or a serial number, model number, and/or firmware revision number of the neuroregulator 104.

The CPU 154 of the neuroregulator 104 also may receive input signals and produce output signals to control a signal generation module 159 of the neuroregulator 104. Signal generation timing may be communicated to the CPU 154 from the external charger 101 via the coil 105 and the telemetry module 155. In other embodiments, the signal generation timing may be provided to the CPU 154 from an oscillator module (not shown). The CPU 154 also may receive scheduling signals from a clock, such as 32 KHz real time clock (not shown).

The CPU 154 forwards the timing signals to the signal generation module 159 when therapy signals are to be produced. The CPU 154 also may forward information about the configuration of the electrode arrangement 108 to the signal generation module 159. For example, the CPU 154 can forward information obtained from the external charger 101 via the coil 105 and the telemetry module 155.

The signal generation module 159 provides control signals to an output module 161 to produce therapy signals. In an embodiment, the control signals are based at least in part on the timing signals received from the CPU 154. The control signals also can be based on the electrode configuration information received from the CPU 154.

The output module 161 produces the therapy signals based on the control signals received from the signal generation module 159. In an embodiment, the output module 161 produces the therapy signals by amplifying the control signals. The output module 161 then forwards the therapy signals to the lead arrangement 108.

In an embodiment, the signal generation module 159 receives power via a first power regulator 156. The power regulator 156 regulates the voltage of the power to a predetermined voltage appropriate for driving the signal generation module 159. For example, the power regulator 156 can regulate the voltage to about 2.5 volts.

In an embodiment, the output module 161 receives power via a second power regulator 160. The second power regulator 160 may regulate the voltage of the power in response to instructions from the CPU 154 to achieve specified constant current levels. The second power regulator 160 also may provide the voltage necessary to deliver constant current to the output module 161.

The output module 161 can measures the voltage of the therapy signals being outputted to the lead arrangement 108 and reports the measured voltage to the CPU 154. A capacitive divider 162 may be provided to scale the voltage measurement to a level compatible with the CPU 154. In another embodiment, the output module 161 can measure the impedance of the lead arrangement 108 to determine whether the leads 106, 106a are in contact with tissue. This impedance measurement also may be reported to the CPU 154.

b. External Charger

Figure 4:
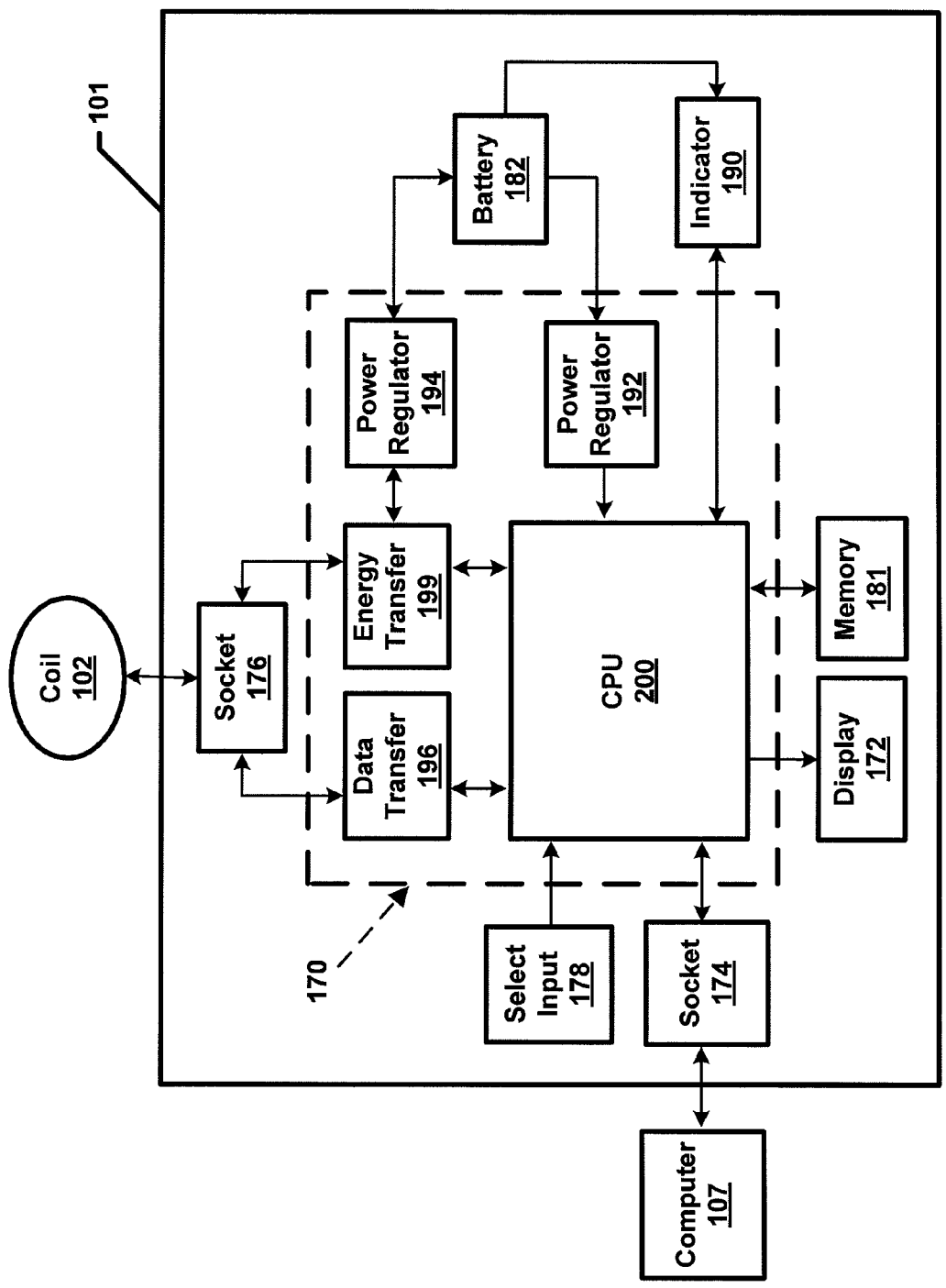
FIG. 4 is a block diagram of a circuit module for an external charger for use in the therapy system of FIG. 1 according to aspects of the present disclosure.

A block diagram view of an example external charger 101 is shown in FIG. 4. The example external charger 101 may cooperate with any of the neuroregulators 104, 104' discussed above to provide therapy to a patient. The external charger 101 is configured to transmit to the neuroregulator 104 (e.g., via an RF link) desired therapy parameters and treatment schedules and to receive data (e.g., patient data) from the neuroregulator 104. The external charger 101 also is configured to transmit energy to the neuroregulator 104 to power the generation of therapy signals and/or to recharge an internal battery 151 of the neuroregulator 104. The external charger 101 also can communicate with an external computer 107.

In general, the external charger 101 includes power and communications circuitry 170. The power and communications circuitry 170 is configured to accept input from multiple sources, to process the input at a central processing unit (CPU) 200, and to output data and/or energy (e.g., via coil 102, socket 174, or display 172). It will be appreciated that it is well within the skill of one of ordinary skill in the art (having the benefit of the teachings of the present invention) to create such circuit components with such function.

For example, the circuit power and communications circuit 170 can be electrically connected to the external coil 102 for inductive electrical coupling to the coil 105 of the neuroregulator 104. The power and communications circuit 170 also can be coupled to interface components enabling input from the patient or an external computing device (e.g., a personal computer, a laptop, a personal digital assistant, etc.) 107. For example, the external charger 101 can communicate with the computing device 107 via an electrically isolated Serial port.

The external charger 101 also includes a memory or data storage module 181 in which data received from the neuroregulator 104 (e.g., via coil 102 and socket input 176), the external computer 107 (e.g., via socket input 174), and/or the patient (e.g. via select input 178) can be stored. For example, the memory 181 can store one or more predetermined therapy programs and/or therapy schedules provided from the external computer 107. The memory 181 also can store software to operate the external charger 101 (e.g., to connect to the external computer 107, to program external operating parameters, to transmit data/energy to the neuroregulator 104, and/or to upgrades the operations of the CPU 200). Alternatively, the external charger 101 can include firmware to provide these functions. The memory 181 also can store diagnostic information, e.g., software and hardware error conditions.

An external computer or programmer 107 may connect to the communications circuit 170 through the first input 174. In an embodiment, the first input 174 is a port or socket into which a cable coupled to the external computer 107 can be plugged. In other embodiments, however, the first input 174 may include any connection mechanism capable of connecting the external computer 107 to the external charger 101. The external computer 107 provides an interface between the external charger 101 and a physician (e.g., or other medical professional) to enable the physician to program therapies into the external charger 101, to run diagnostic and system tests, and to retrieve data from the external charger 101.

The second input 176 permits the external charger 101 to couple selectively to one of either an external power source 180 or the external coil 102 (see FIG. 1). For example, the second input 176 can define a socket or port into which the power source 180 or external coil 102 can plug. In other embodiments, however, the second input 176 can be configured to couple to a cable or other coupling device via any desired connection mechanism. In one embodiment, the external charger 101 does not simultaneously connect to both the coil 102 and the external power source 180. Accordingly, in such an embodiment, the external power source 180 does not connect directly to the implanted neuroregulator 104.

The external power source 180 can provide power to the external charger 101 via the second input 176 when the external charger 101 is not coupled to the coil 102. In an embodiment, the external power source 180 enables the external charger 101 to process therapy programs and schedules. In another embodiment, the external power source 180 supplies power to enable the external charger 101 to communicate with the external computer 107 (see FIG. 1).

The external charger 101 optionally may include a battery, capacitor, or other storage device 182 (FIG. 4) enclosed within the external charger 101 that can supply power to the CPU 200 (e.g., when the external charger 101 is disconnected from the external power source 180). The power and communications circuit 170 can include a power regulator 192 configured to receive power from the battery 182, to regulate the voltage, and to direct the voltage to the CPU 200. In a preferred embodiment, the power regulator 192 sends a 2.5 volt signal to the CPU 200.

The battery 182 also can supply power to operate the external coil 102 when the coil 102 is coupled to the external charger 101. The battery 182 also can supply power to enable the external charger 101 to communicate with the external computer 107 when the external power source 180 is disconnected from the external charger 101. An indicator 190 may provide a visual or auditory indication of the remaining power in the battery 182 to the user.

In an embodiment, the battery 182 of the external charger 101 is rechargeable. For example, the external power source 180 may couple to the external charger 101 to supply a voltage to the battery 182. In such an embodiment, the external charger 101 then can be disconnected from the external power source 180 and connected to the external coil 102 to transmit power and/or data to the neuroregulator 104. Further details regarding example rechargeable systems include U.S. Pat. No. 6,516,227 to Meadows, issued Feb. 4, 2003; U.S. Pat. No. 6,895,280 to Meadows, issued May 17, 2005; and U.S. patent application Publication No. US 2005/0107841 to Meadows May 19, 2005, the disclosures of which are hereby incorporated herein by reference.

In an alternative embodiment, the battery 180 is a replaceable, rechargeable battery, which is recharged external to the external charger 101 in its own recharging stand. In yet another embodiment, the battery 182 in the external charger 101 can be a replaceable, non-rechargeable battery.

In use, energy from the external power source 180 flows through the second input 176 to an energy transfer module 199 of the power and communications circuit 170. The energy transfer module 199 directs the energy either to the CPU 200 to power the internal processing of the external charger 101 or to the battery 182. In an embodiment, the energy transfer module 199 first directs the energy to a power regulator 194, which can regulate the voltage of the energy signal before sending the energy to the battery 182.

In some embodiments, the external coil 102 of the external charger 101 can supply energy from the battery 182 to the internal coil 105 of the neuroregulator 104 (e.g., to recharge the internal power source 151 (FIG. 3) of the neuroregulator 104). In such embodiments, the energy transfer module 199 receives power from the battery 182 via the power regulator 194. For example, the power regulator 194 can provide a sufficient voltage to activate the energy transfer module 199. The energy transfer module 199 also can receive instructions from the CPU 200 regarding when to obtain power from the battery 182 and/or when to forward power to the external coil 102. The energy transfer module 199 delivers the energy received from the battery 182 to the coil 102 of the external charger 101 in accordance with the instructions provided by the CPU 200. The energy is sent from the external coil 102 to the internal coil 105 of the neuroregulator 104 via RF signals or any other desired power transfer signal. In an embodiment, therapy delivery at the neuroregulator 104 is suspended and power is delivered from the external charger 101 during recharging of the internal power source 151.

In some embodiments, the external charger 101 controls when the internal battery 151 of the implanted neuroregulator 104 is recharged. For example, the external charger 101 can determine when to recharge the battery 151 using the processes described in U.S. Pat. No. 6,895,280 to Meadows issued May 17, the disclosure of which is hereby incorporated herein by reference. In other embodiments, however, the implanted neuroregulator 104 controls when the battery 151 is recharged. Details pertaining to controlling the battery recharging process can be found in U.S. Pat. No. 3,942,535 to Schulman, issued Mar. 9, 1976; U.S. Pat. No. 4,082,097 to Mann, issued Apr. 4, 1978; U.S. Pat. No. 5,279,292 to Baumann, issued Apr. 4, 1978; and U.S. Pat. No. 6,516,227 to Meadows, issued Feb. 4, 2003, the disclosures of which are hereby incorporated herein by reference. These details typically parallel the battery manufacturer's recommendations regarding how to charge the battery.

As noted above, in addition to power transmissions, the external coil 102 also can be configured to receive data from and to transmit programming instructions to the neuroregulator 104 (e.g., via an RF link). A data transfer module 196 may receive and transmit data and instructions between the CPU 200 and the internal coil 105. In an embodiment, the programming instructions include therapy schedules and parameter settings. Further examples of instructions and data transmitted between the external coil 102 and the implanted coil 105 are discussed in greater detail herein.

Figure 5:
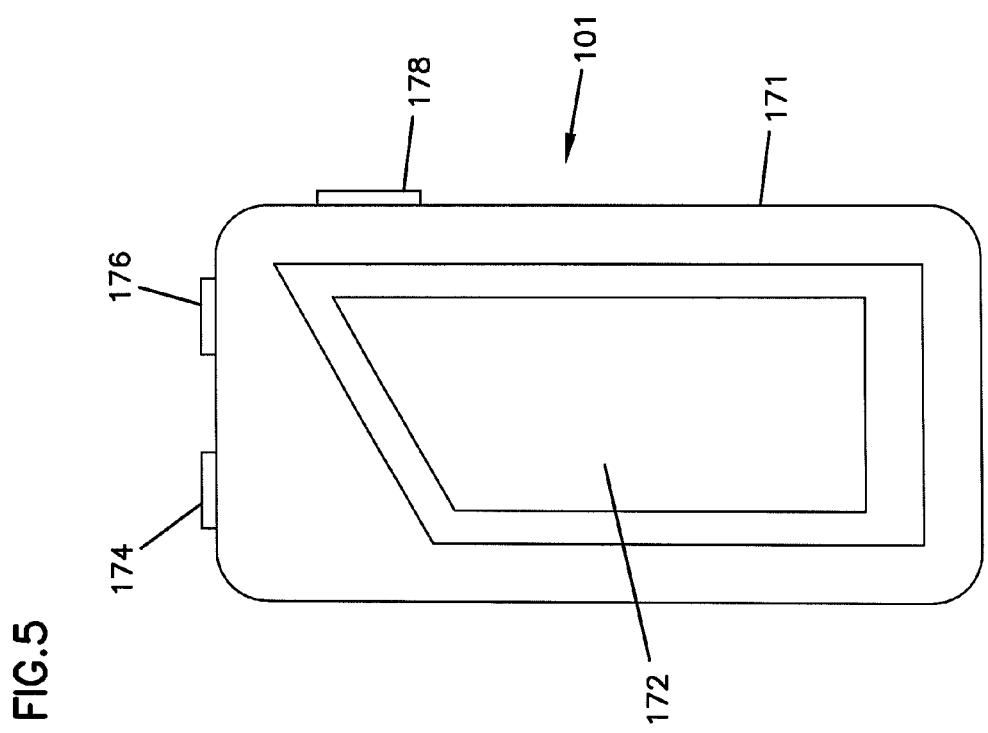
FIG. 5 is a plan schematic view of an example external charger for use in the therapy system of FIG. 1 according to aspects of the present disclosure.

FIG. 5 shows a front view of an example external charger 101. The external charger 101 includes a housing 171 defining a first input (e.g., socket input) 174, a second input (e.g., socket input) 176, and a third input (e.g., select input) 178 coupled to the communications circuit 170. In an embodiment, the housing 171 also may enclose a battery 182 configured to supply power to the external charger 101 via the power and communications circuit 170. Alternatively, the external charger 101 can receive power from an external source 180 (FIG. 1).

As shown in FIG. 5, visual display 172 also is provided on the housing 171 for presenting human readable information processed by the communications circuit 170. In an embodiment, the visual display 172 is a liquid crystal display (LCD) screen. In other embodiments, however, the visual display 172 can include any display mechanism (e.g., a light-emitting diode (LED) screen, vacuum fluorescent display (VFD) screen, etc.). Non-limiting examples of information that can be shown on the visual display 172 include the status of the battery 182 of the external charger 101, the status of the battery 151 in the implanted neuroregulator 104, coil position (as will be described), impedances between the electrodes 212, 212a and attached tissue, and error conditions.

As shown in FIG. 5, the third input 178 of the external charger 101 includes a selection input 178 with which the user can interact with the external charger 101. In an embodiment, the selection input 178 can include a button, which sequentially selects menu options for various operations performed by the external charger 101 when pressed successively. In other embodiments, however, the third input 178 includes another type of selection input (e.g., a touch screen, a toggle-switch, a microphone for accepting voice-activated commands, etc.).

Example functions capable of selection by the user include device reset, interrogation of battery status, interrogation of coil position, and/or interrogation of lead/tissue impedance. In other embodiments, a user also can select measurement of tissue/lead impedance and/or initiation of a stomach contraction test. Typically, the measurement and testing operations are performed when the patient is located in an operating room, doctor's office, or is otherwise surrounded by medical personnel.

In another embodiment, the user can select one or more programs and/or therapy schedules to submit to the memory 152 of the neuroregulator 104. For example, the user can cycle through available programs by repeatedly pressing the selection button 178 on the external charger 101. The user can indicate the user's choice by, e.g., depressing the selector button 178 for a predetermined period of time or pressing the selector button 178 in quick succession within a predetermined period of time.

In use, in some embodiments, the external charger 101 may be configured into one of multiple modes of operation. Each mode of operation can enable the external charger 101 to perform different functions with different limitations. In an embodiment, the external charger 101 can be configured into five modes of operation: an Operating Room mode; a Programming mode; a Therapy Delivery mode; a Charging mode; and a Diagnostic mode.

When configured in the Operating Room mode, the external charger 101 can be used to determine whether the implanted neuroregulator 104 and/or the implanted lead arrangement 108 are functioning appropriately. If any component of the therapy system 100 is not functioning as desired, then the medical personnel can trouble-shoot the problem while still in the operation room or can abandon the procedure, if necessary.

For example, the external charger 101 can be used to determine whether the impedance at the electrodes 212, 212a of the lead arrangement 108 (FIG. 1) is within a prescribed range. When the impedance is within the prescribed range, a gastric contraction test can be initiated to demonstrate that the electrodes 212, 212a are appropriately positioned and can become active. If the impedance is outside an acceptable range, the system integrity can be checked (e.g. connections to the leads can be verified). Additionally, the therapy electrodes 212, 212a may be repositioned to provide better electrode-tissue contact.

In another embodiment, the external charger 101 can be used to initiate a stomach contraction test in the operating room. The stomach contraction test enables medical personnel to confirm the electrodes 212, 212a of the lead arrangement 108 (FIG. 1) are in contact with the appropriate nerves and not with some other tissue. For example, the external charger 101 can instruct the neuroregulator 104 to generate a signal tailored to cause the stomach to contract if the signal reaches the appropriate nerves.

Typically, the external charger 101 is not connected to an external computer 107 when configured in the Operating Room mode. In a preferred embodiment, the external charger is connected (e.g., via socket input 176) to a physician coil 102' (shown schematically in FIG. 6) instead of a patient coil 102 (described above). The physician coil 102' can differ from the patient coil 102 in one or more respects.

Figure 6:
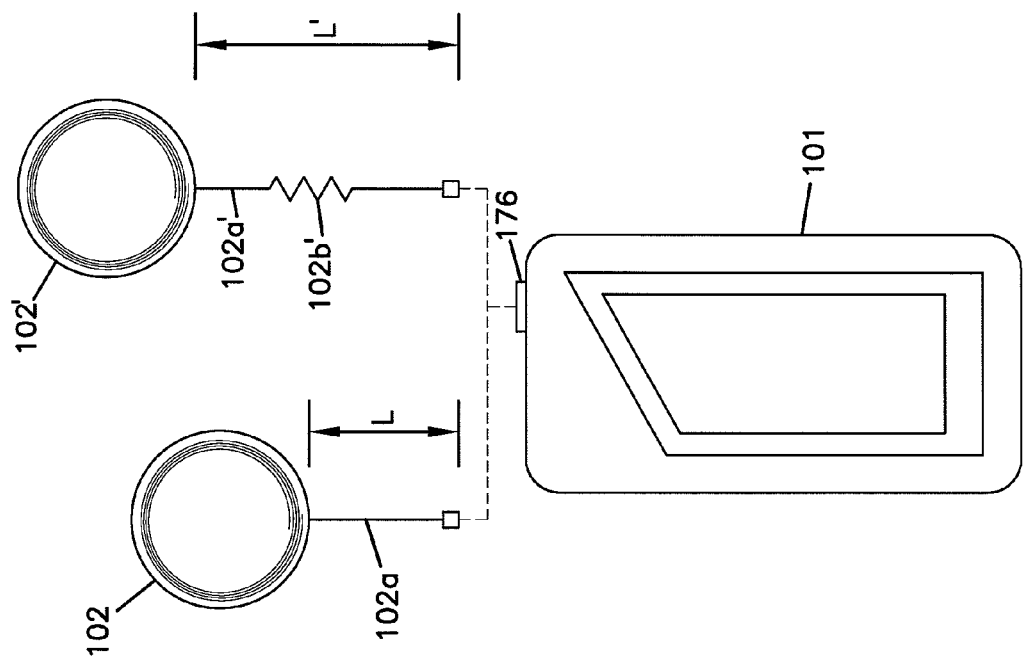
FIG. 6 is a plan, schematic view of an external charger and schematic views of a patient transmit coil and a physician transmit coil configured to couple to the external charger according to aspects of the present disclosure.

For example, as shown in FIG. 6, a length L' of the connection cable 102a' on the physician coil 102' can be longer than a length L of the cable 102a of the patient coil 102. In one example embodiment, the length L' of the connection cable 102a' of the physician coil 102' can be about 300 cm and the length L of the connection cable 102a of the patient coil 102 can be about 60 cm. The longer length L' allows the external charger 101 to be located outside the sterile field in the operating room when the physician coil 102' is connected.

In another embodiment, the physician coil 102' can include an indicator circuit to identify the coil 102' as a physician coil to the external charger 101. For example, the physician coil 102' can contain a small resistor 102b', which can be recognized by the external charger 101 when the physician coil 102' is plugged into the socket 176. When the external charger 101 detects the presence of the indicator circuit, the external charger 101 automatically configures itself into an Operating Room mode. This mode allows the physician to conduct various system and patient response tests, such as those described above, without the need for connection to a clinician computer 107.

When configured in the Programming mode, the external charger 101 is connected with the external computer 107 (FIG. 1) via which the physician manages the components of the therapy system 100. In general, the physician may select a therapy program and a therapy schedule stored on the external computer 107 to transfer to the external charger 101. In certain embodiments, the external charger 101 forwards the programs and schedule to the neuroregulator 104. In an embodiment, the external charger 101 can be coupled to the physician coil 102' during programming. In another embodiment, the external charger 101 can be coupled to the patient coil 102. In addition, in different embodiments, the external computer 107 also can assess the impedance of the electrodes 212, 212a, initiate system and/or diagnostic tests, and take corrective action when the external charger 101 is configured into the Programming mode.

After the neuroregulator 104 has been implanted and the external charger 101 and/or neuroregulator 104 have been programmed, the external charger 101 can be configured into the Therapy Delivery mode. When configured in the Therapy Delivery mode, the external charger 101 communicates with and/or powers the neuroregulator 104 as described above. Typically, the external charger 101 is coupled to the patient coil 102 and not to the external computer 107 when configured in the Therapy Delivery mode.

The external charger 101 also can interact with the user via the third input (e.g., the selector button) 178 and the display 172 to select the therapy to be provided. In an embodiment, the external charger 101 can send instructions indicating which program the neuroregulator 104 should follow while administering therapy. In another embodiment, the external charger 101 sends instructions in accordance with a selected program stored on the external charger 101.

If the neuroregulator 104 includes an internal power source 151, then the external charger 101 can enter a Charging mode in which the external charger 101 recharges the internal power source 151 of the neuroregulator 104 when the neuroregulator 104 is not delivering therapy. Typically, the external charger 101 enters the Charging mode at the request of the neuroregulator 104. In a preferred embodiment, the neuroregulator 104 controls how much power is sent by the external charger 101.

During follow-up visits between the patient and the physician, the external charger 101 may be configured into a Diagnostic mode. In this mode, the external charger 101 is coupled to the external computer 107 to provide an interface for the physician to obtain data stored on the external charger 101 and to download therapy and/or software updates. In an embodiment, the display 172 on the external charger 101 is disabled and all information is conveyed to the physician via the external computer 107 only. The external charger 101 may be coupled to either coil 102, 102' when configured in the Diagnostic mode.

In an embodiment, the external charger 101 also can be configured into a Shipping mode, in which the battery 182 is disconnected from the rest of the circuitry. The Shipping mode avoids draining the battery 182 and enhances safety. In one such embodiment, pressing the selector button 172 causes the external charger 101 to change from this Shipping mode into another mode, such as the Therapy Delivery mode.

c. Alignment of External and Implanted Coils

The external charger 101 enables alignment of the relative positions of the external and implanted coils 102, 105 and optimization of the signal strength. Optimizing the alignment of the coils 102, 105 and the power of the transmission signal facilitates continuous, transcutaneous transmission of power and/or information.

i. Positioning of External Coil

In general, the external coil 102 is adapted to be placed on the patient's skin (e.g., by adhesives) overlying the implanted internal coil 105. The position and orientation of the coils 102, 105 can affect signal reliability. In addition, the strength of the transmission signals between the external coil 102 and the implanted coil 105 also is affected by the distance between the coils 102, 105. Implanting the neuroregulator 104 very close to the surface of the skin 103 typically results in a large and expanded range of signal strengths. Conversely, implanting the neuroregulator 104 at a large distance beneath the skin 103 yields a generally weak transmission link and a compressed range of signal strengths.

Figure 7:
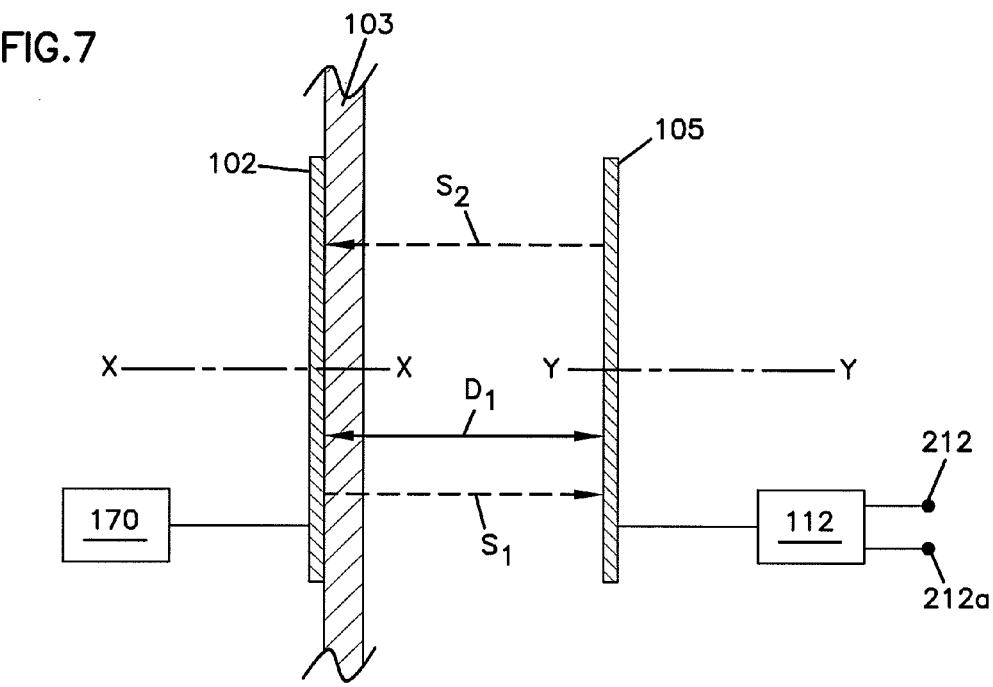
FIG. 7 is a side elevation, schematic view of an external coil in a desired alignment over an implanted coil according to aspects of the present disclosure.

FIG. 7 illustrates an external coil 102 appropriately aligned with an implanted coil 105. The coil 105 is implanted beneath the skin 103 at a preferred depth $D_1$ (e.g., about two centimeters to about three centimeters beneath the skin 103). Preferably, a plane of the coil 105 extends parallel to the surface of the skin 103. In an embodiment, each coil 102, 105 is a circular coil surrounding a central axis X-X, Y-Y, respectively. As shown in FIG. 7, in a preferred alignment configuration, the axes X-X, Y-Y are collinear so that there is no lateral offset of the axes X-X, Y-Y and the planes of the coils 102, 105 are parallel to one another. Such an alignment configuration may be attained, e.g., when the external coil 102 is applied to a patient's skin 103 when the patient is lying flat (e.g., on the patient's back).

Figure 8:
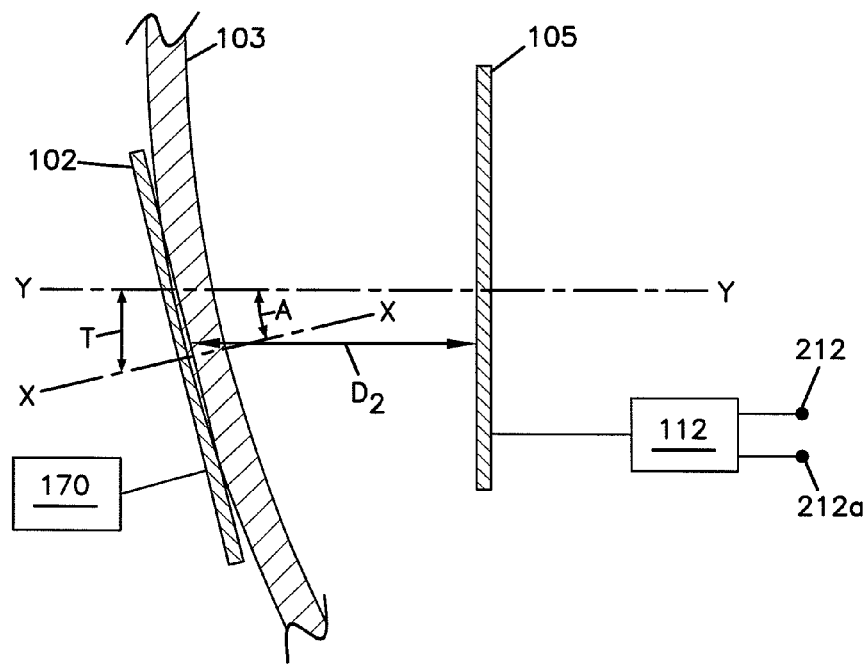
FIG. 8 illustrates the external coil and implanted coil of FIG. 7 arranged in a misaligned position according to aspects of the present disclosure.

FIG. 8 illustrates misalignment between the coils 102, 105 resulting from movement of the patient (e.g., a change in posture). For example, when the patient sits, excess fat may cause the skin 103 to roll. This rolling may cause the spacing between the coils 102, 105 to increase to a distance D2. Also, the orientation of the external coil 102 may change so that the axes X-X and Y-Y of the coils 102, 105, respectively, have a lateral offset T and an angular offset A. Such changes in spacing and orientation may be occurring constantly throughout the day.

The relative position of the coils 102, 105 may be optimized (e.g., for each use) when the external charger 101 senses the transmission link is weakened (e.g., on initial power up or when the energy transfer to the implantable neuroregulator 104 has degraded). For example, the external charger 101 can sound an alarm and invite the user to configure the external charger 101 into a Locate mode. Alternatively, the user can decide independently to enter the Locate mode (e.g., through a menu selection).

When configured in the Locate mode, the external charger 101 prompts the user to adjust the orientation of the external coil 102 to achieve an alignment (e.g., coaxial alignment) facilitating better coil interaction. The external charger 101 also provides feedback to the user indicating the current degree of alignment of the coils 102, 105. Examples of such feedback include audio signals, lit LED's, bar graphs or other textual, graphical, and/or auditory signals provided to the user.

In general, when the external charger 101 is configured in the Locate mode, the user sweeps the external coil 102 back and forth across the general location of the implanted neuroregulator 104. During the sweep, the external charger 101 sends a locator signal $S_1$ to the implanted coil 105 (see FIG. 7). The implanted coil 105 responds with a feedback signal $S_2$ (FIG. 7). The external charger 101 analyzes the feedback signal $S_2$ to determine the strength of the transmission link between the coils 102, 105.

In an embodiment, the external charger 101 keeps track of the strongest and weakest signals found during the sweep. The maximum signal strength and the minimum signal strength can be indicated to the user, e.g., via the visual display 172. These maximum and minimum values provide the user with context for judging the relative strength of a given signal at each location during the sweep. In an embodiment, the relative strength of the signal at a given position also can be displayed to the user as the user passes the external coil 102 over the position.

For example, in one embodiment, the first signal may be indicated initially as the maximum and minimum signal strength on the visual display 172. As the external coil 102 is moved about, any subsequent signals having greater signal strength replace the maximum signal shown. The strength of any subsequent, weaker signal also can be tracked by the external charger 101. The strength of the weakest signal can be indicated to the user as the minimum signal strength found. In one embodiment, if the strength of a subsequent signal falls between the currently established values for minimum and maximum, then an interpolated value representing the relative strength of the signal at the respective coil position can be displayed.

Thus the external charger 101 learns the maximum and minimum values for signal strength pertaining to external coil positions relative to the location of the implanted coil 105. By identifying the context of the signal strength measurements (i.e., the maximum and minimum signal strength found during a sweep), the external charger 101 can provide consistent and context-sensitive measurements of signal strength to the user regardless of the distance of the coil 102 from the implanted coil 105. Such measurements facilitate identification of an optimum coil position.

After the initial placement, the external coil 102 may need to be repositioned with respect to the implanted coil 105 to maintain the signal integrity. The external charger 101 can monitor whether the neuroregulator 104 is receiving signals having sufficient signal strength. If the external charger 101 determines the neuroregulator 104 is not receiving a sufficient signal, then the external charger 101 may sound an alarm (e.g., auditory and/or visual) to alert the user that coil transmission effectiveness has been lost.

In an embodiment, after indicating the loss of transmission effectiveness, the external charger 101 may invite the user to configure the external charger 101 into the Locate mode to reposition the external coil 102. Alternatively, the external charger 101 may invite the user to modify the position of the external coil 102 without entering the Locate mode. In an embodiment, when the coil transmission effectiveness is re-established, the system automatically self-corrects and resumes therapy delivery.

ii. Dynamic Signal Power Adjustment

The amount of power received at the neuroregulator 104 can vary due to relative movement of the coils 102, 105 after the initial placement of the external coil 102. For example, the signal strength may vary based on the distance between coils 102, 105, the lateral alignment of the coils 102, 105, and/or the parallel alignment of the coils 102, 105. In general, the greater the distance between the coils 102, 105, the weaker the transmission signal will be. In extreme cases, the strength of the transmission signal may decrease sufficiently to inhibit the ability of the neuroregulator 104 to provide therapy.

The coils 102, 105 may move relative to one another when the patient moves (e.g., walks, stretches, etc.) to perform everyday activities. Furthermore, even when the patient is inactive, the external coil 102 may be placed on tissue with substantial underlying fat layers. The surface contour of such tissue can vary in response to changes in patient posture (e.g., sitting, standing, or lying down). In the treatment of obesity, the distance from the top layer of skin 103 to the implanted coil 105 can vary from patient to patient. Moreover, the distance can be expected to vary with time as the patient progresses with anti-obesity therapy.

In addition, the power consumption needs of the neuroregulator 104 can change over time due to differences in activity. For example, the neuroregulator 104 will require less power to transmit data to the external charger 101 or to generate therapy signals than it will need to recharge the internal battery 151.

To overcome these and other difficulties, an embodiment of the external charger 101 can change the amplification level of the transmission signal (e.g., of power and/or data) to facilitate effective transmission at different distances between, and for different relative orientations of, the coils 102, 105. If the level of power received from the external charger 101 varies, or if the power needs of the neuroregulator 104 change, then the external charger 101 can adjust the power level of the transmitted signal dynamically to meet the desired target level for the implanted neuroregulator 104.

Adjustments to the power amplification level can be made either manually or automatically. In an embodiment, the external charger 101 may determine a target strength of the transmission signal (e.g., a predetermined strength selected to provide sufficient power to the neuroregulator 104), assess the effectiveness of the transmission signals currently being sent to the implanted coil 105, and automatically adjust the amplification levels of the transmitted signals to enhance the effectiveness of the transmissions between the external coil 102 and the implanted coil 105.

For example, if the neuroregulator 104 indicates it is recharging its battery 151, then the external charger 101 may establish a transmission link having a first power level appropriate for the task. At the conclusion of recharging, and when the neuroregulator 104 subsequently indicates it will begin therapy delivery, then the external charger 101 may change the power of the transmission link to a second power level sufficient to initiate therapy generation and delivery.

The external charger 101 also may increase the power level of the signal if the signal is lost due to separation and/or misalignment of the coils. If the external charger 101 is unable to sufficiently increase the power level of the transmitted signal, however, then the external charger 101 may issue an alarm and/or an invitation to the user to reposition the external coil 102 as described above.

The external charger 101 also may decrease the strength of the signal (i.e., the amount of power) being sent to the neuroregulator 104. For example, due to safety concerns, the amount of power that can be transmitted across skin via RF signals is limited. Receiving excessive amounts of power could cause the neuroregulator 104 to heat up and potentially burn the patient.

In an embodiment, the neuroregulator 104 includes a temperature sensor (not shown) configured to monitor the temperature of the neuroregulator 104. The neuroregulator 104 can communicate the temperature to the external charger 101. Alternatively, the neuroregulator 104 can issue a warning to the external charger 101 if the neuroregulator 104 becomes too warm. When the temperature of the neuroregulator 104 is too high, the external charger 101 may lower the power transmitted to the implanted coil 105 of the neuroregulator 104 to bring the temperature down to an acceptable level. Alternatively, the neuroregulator 104 may detune its receiving RF input circuit 157 to reduce power and temperature.

In a preferred embodiment, the temperature of the neuroregulator 104 should not exceed the surface temperature of the surrounding skin by greater than about 2° C. (assuming a normal body temperature of 37° C.). Operational parameters, such as current, frequency, surface area, and duty cycle, also can be limited to ensure safe operation within the temperature limit. Further details regarding safety concerns pertaining to transdermal power transmission can be found, e.g., in *The Cenelec European Standard*, EN 45502-1 (August 1997), page 18, paragraph 17.1, the disclosure of which is hereby incorporated by reference herein.

In an embodiment, the external charger 101 also can decrease the target power level based on a "split threshold" power delivery concept. In such an embodiment, the external charger 101 initially provides a stronger signal than necessary to the neuroregulator 104 to ensure sufficient power is available. The external charger 101 then reduces the strength of the transmissions to a level just above the necessary signal strength when the actual requirements have been established. This subsequent reduction in power saves drain on the external battery 182 or power source 180.

For example, the external charger 101 can provide a low level of power capable of sustaining basic operation of the neuroregulator 104 when the neuroregulator 104 indicates it is not actively providing therapy or recharging its battery 151. When the neuroregulator 104 indicates it is about to initiate therapy, however, the external charger 101 can increase the power level of the transmission signal to a first threshold level, which is comfortably in excess of the power required to provide basic operation of the neuroregulator 104 as well as provide therapy. When the actual power requirements for therapy delivery become apparent, the external charger 101 may decreases the power level of the signal to a second threshold level, which is closer to the minimum power level required to provide basic functionality and maintain therapy delivery.

To perform this dynamic adjustment of signal strength, the external charger 101 analyzes a feedback signal (e.g., signal $S_2$ of FIG. 7) received from the implanted neuroregulator 104 indicating the amount of power required by the neuroregulator 104. The signal $S_2$ also may provide information to the external charger 101 indicating the power level of the signal $S_1$ being received by the implanted coil 105 of the neuroregulator 104. Such signal analysis would be within the skill of one of ordinary skill in the art (having the benefit of the teachings of the present invention).

In an embodiment, the external charger 101 sets the signal power level based on a predetermined target power level for the transmission signal $S_1$. In response to the feedback signal $S_2$, the external charger 101 modifies the power level of the transmission signal $S_1$ to be within a tolerance range of the target power level. In an embodiment, the external charger 101 iteratively modifies the power level of the transmission signal $S_1$ until the feedback signal $S_2$ indicates the power level is within the tolerance range.

In addition to the dynamic adjustment of transmitted signal power described above, the neuroregulator 104 can be configured to optimize the power received from the external charger 101 when the neuroregulator 104 is recharging its battery 151. For example, the neuroregulator 104 may tune (e.g., using a combination of hardware and software) the natural resonant frequency of a recharging circuit (not shown) to maximize the power delivered to a load resistance for a given set of input parameters such as voltage, current and impedance at the implanted coil 105.

Transmission of power and/or information between the external charger 101 and the implanted neuroregulator 104 is typically performed using a carrier frequency of 6.78 MHz. Emission requirements of industrial, scientific and medical equipment are governed by Federal Communications Commission requirements described in FCC Title 47, Parts 15 and 18, and in EN 55011. The FCC requirements in the vicinity of this frequency are more restrictive than those of EN 55011.

A preferred method for managing the temperature and carrier frequency of the neuroregulator 104 during the recharging process includes passing a high power unmodulated transmission between the external charger 101 and the implantable neuroregulator 104 for a finite time (e.g., from about half of a minute to about five minutes), during which time no informational communication takes place between the external charger 101 and the implantable neuroregulator 104 (i.e., no information is passed between the charger 101 and the neuroregulator 104). At the conclusion of this finite time period, the unmodulated transmission ceases.

An informational, modulated communicational transmission then is passed at low power (e.g., within the requirements of FCC Title 47 Part 15) during which the temperature of the implantable neuroregulator 104 is communicated periodically to the external charger 101. If the temperature rises within certain restrictions (e.g., within the restrictions of *The Cenelec European Standard*, EN 45502-1 (August 1997), page 18, paragraph 17.1), then the communications transmission may be terminated, and the whole cycle may be repeated beginning with the initiation of the high power, unmodulated, recharging transmission.

In an additional preferred embodiment, when the informational, modulated communicational transmission is performed, the requisite signal power is reduced by using only externally transmitted power for the telemetered communications, and by simultaneously using internal battery power to operate the rest of the implanted circuitry 112 (FIGS. 3A and 3B), such as a microcontroller and/or peripherals. In such embodiments, the transmitted power may be less than if implant components (microcontroller and/or peripherals) also were receiving power from the RF transmission. Accordingly, the transmitted power may be limited to the power required for communications at short distances of six centimeters or less. Advantageously, such a power reduction reduces the total power required to below FCC Part 15 limits for telemetry communications.

During the phase in which the battery 151 of the implantable neuromodulator 104 is being recharged by a high powered, unmodulated transmission (e.g., under the requirements of FCC Title 47 Part 18), the temperature of the implanted neuroregulator 104 may be monitored and, if necessary, steps taken to inhibit the temperature from exceeding certain requirements (e.g., the requirements of *The Cenelec European Standard*, EN 45502-1 (August 1997), page 18, paragraph 17.1). For example, the temperature may be reduced by terminating the high powered, unmodulated transmission. In an alternative embodiment, the power level of the high powered, unmodulated transmission may be reduced in later cycles to limit the increase in temperature. In another embodiment, a control loop is established between the temperature rise and the power level of the unmodulated transmission to ensure the increase in temperature always remains within the identified requirements.

d. Implanted Leads

Figure 9:
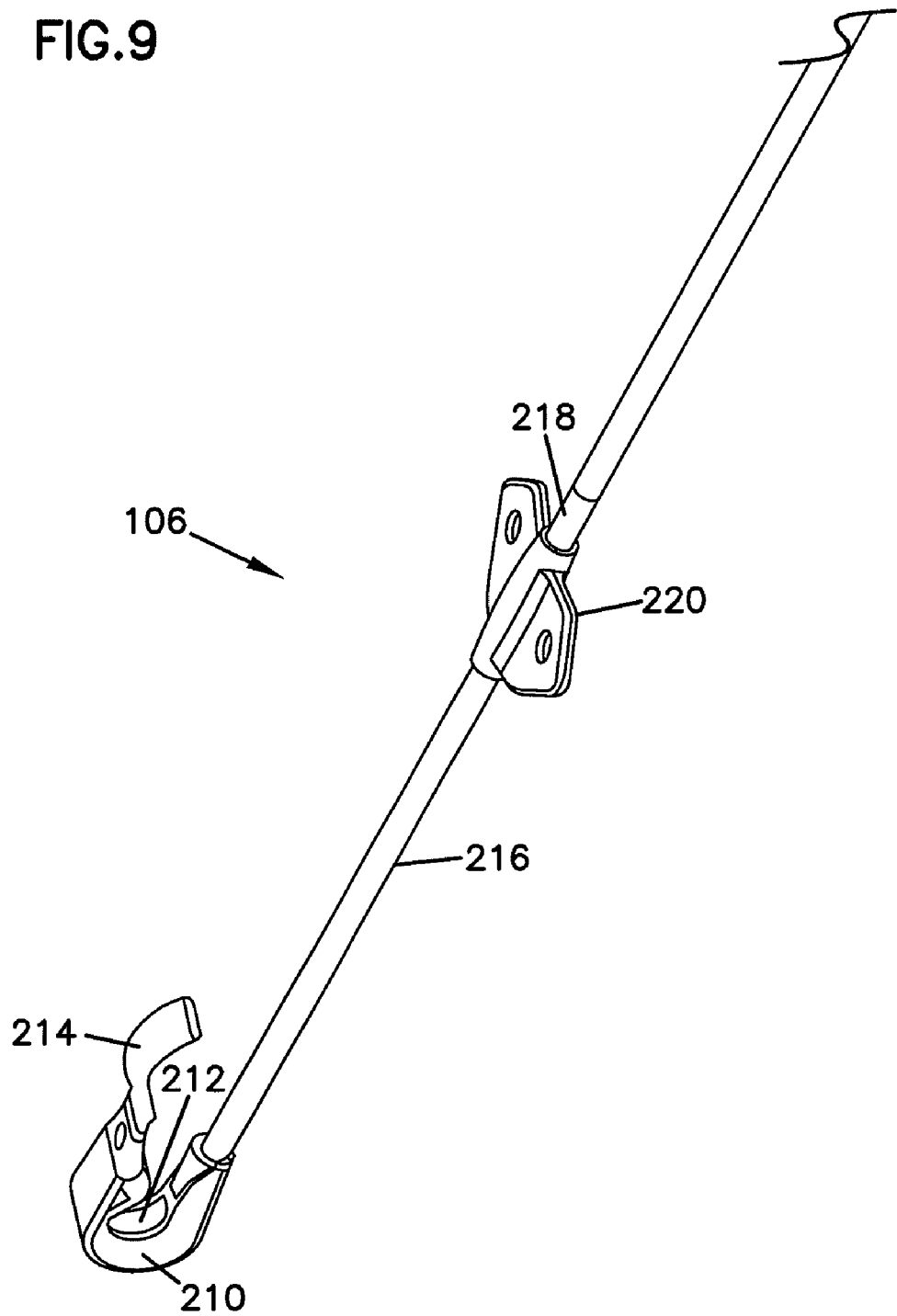
FIG. 9 is a perspective view of a distal portion of a bipolar therapy lead according to aspects of the present disclosure.

FIG. 9 shows an example distal end of a bipolar lead, such as lead 106 (see FIG. 1). The lead 106 includes a lead body 210 curved to receive a nerve (e.g., a vagus nerve). The lead body 210 contains an exposed tip electrode 212 configured to contact with the nerve received within the lead body 210. The tip electrode 212 is capable of delivering an electrical charge to nerves having a diameter ranging from about one millimeter to about four millimeters.

The lead body 210 also can have a suture tab 214 to attach the lead body 210 to the patient's anatomy to stabilize the position of the lead body 210. A first end of a flexible lead extension 216, which encloses a conductor from the electrode 212, couples with the lead body 210. A second, opposite end of the lead extension 216 terminates at a pin connector (not shown) for attachment to a connector (e.g., an IS-1 connector) 122 (shown in FIG. 1).

The lead 106 shown in FIG. 9 also includes a ring electrode 218 surrounding the lead extension 216 at a position spaced from the tip electrode 212. In an embodiment, the surface area of each electrode 212, 218 is greater than or equal to about thirteen square millimeters. A suture tab 220 may be provided for placement of the ring electrode 218 on the patient's anatomy in general proximity to the placement of the tip electrode 212 on the nerve.

In an alternative embodiment, a monopolar lead (not shown) may be implanted instead of the bipolar lead 106. Typically, the monopolar lead is the same as the bipolar lead 106, except the monopolar lead lacks a ring electrode 218. Such a monopolar lead is described in commonly assigned and co-pending U.S. patent application Ser. No. 11/205,962, to Foster et al, filed Aug. 17, 2005, the disclosure of which is hereby incorporated by reference.

Further details pertaining to example electrode placement and application of treatment can be found, e.g., in U.S. Pat. No. 4,979,511 to Terry, Jr., issued Dec. 25, 1990; U.S. Pat. No. 5,215,089 to Baker, Jr., issued Jun. 1, 1993; U.S. Pat. No. 5,251,634 to Weinberg, issued Oct. 12, 1993; U.S. Pat. No. 5,531,778 to Maschino et al., issued Jul. 2, 1996; and U.S. Pat. No. 6,600,956 to Maschino et al., issued Jul. 29, 2003, the disclosures of which are hereby incorporated by reference herein.

2. Placement of Electrodes and Electrode Configuration Options

Figure 10:
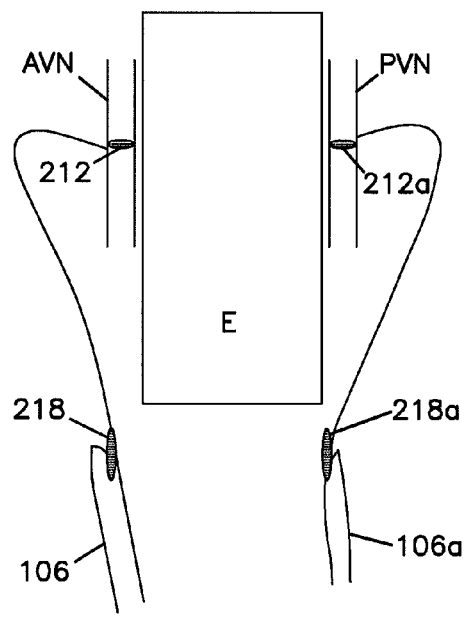
FIG. 10 is a schematic representation of an electrode placement for a blocking therapy according to aspects of the present disclosure.

FIG. 10 shows a posterior vagus nerve PVN and an anterior vagus nerve AVN extending along a length of a patient's esophagus E. The posterior nerve PVN and the anterior AVN are generally on diametrically opposite sides of the esophagus E just below the patient's diaphragm (not shown). A first tip electrode 212 of a lead arrangement 108 (FIG. 1) is placed on the anterior vagus nerve AVN. A second electrode 212a of the lead arrangement 108 is placed on the posterior vagus nerve PVN. The electrodes 212, 212a are connected by leads 106, 106a to a neuroregulator 104 (FIG. 1).

At the time of placement of the leads 106, 106a, it may be advantageous for the tip electrodes 212, 212a to be individually energized with a stimulation signal selected to impart a neural impulse to cause a detectable physiological response (e.g., the generation of antropyloric waves). The absence of a physiological response may indicate the absence of an overlying relation of the tested electrode 212, 212a to a vagus nerve PVN, AVN. Conversely, the presence of a physiological response may indicate an overlying relation (e.g., correct placement) of the tested electrode 212, 212a to a vagus nerve. After determining the leads 106, 106a create a physiologic response, the electrodes 212, 212a can be attached to the nerves PVN, AVN.

A preferred embodiment of the leads 106, 106a for treating obesity is shown in FIG. 10. The lead arrangement 108 includes bipolar leads 106, 106a. The bipolar leads 106, 106a each include one tip (i.e., or cathode) electrode 212, 212a that can be placed directly on the nerve PVN, AVN and one ring (i.e., or anode) electrode 218, 218a that is not placed on the nerve PVN, AVN, but rather may be attached to another structure (e.g., the stomach). In other embodiments, however, the lead arrangement 108 may include monopolar leads (i.e., each lead 106, 106a having only a tip electrode 212, 212a).

Electrical connection between the neuroregulator 104 and the therapy leads 106, 106a is made through bipolar IS-1 compatible lead adapters 122, 122a attached to the neuroregulator 104. If the bipolar lead design is used, two bipolar electrode pairs—one for the anterior vagus and one for the posterior vagus—are provided. One bipolar lead feeds a bipolar electrode pair. If the monopolar lead design is used, only the conductor connected to the distal tip electrode of each bipolar IS-1 connector is used.

The therapies as previously described could be employed by using blocking electrodes or stimulation electrodes or both in order to down-regulate and/or up-regulate the vagus nerve. A blocking signal down-regulates a level of vagal activity and simulates, at least partially, a reversible vagotomy.

Referring to FIGS. 11-18, the pacing signals to the electrodes 212, 212a can be selected to create different types of signals and signal paths (referred to herein as "configurations"). FIGS. 11-18 illustrate four different electrode configurations.

a. Blocking Electrode Configuration (1)

Figure 11:
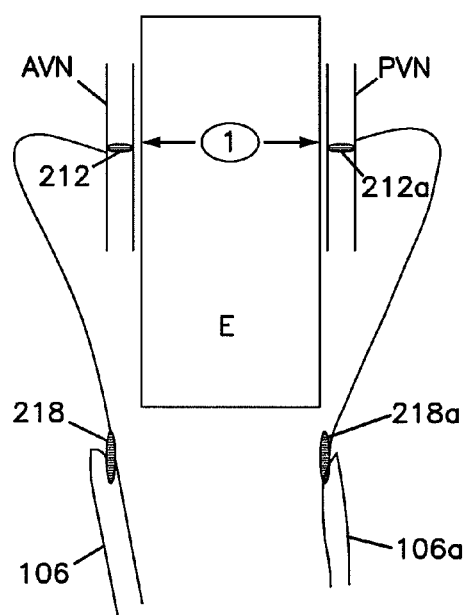
FIG. 11 is a schematic representation of a first electrode configuration according to aspects of the present disclosure.
Figure 12:
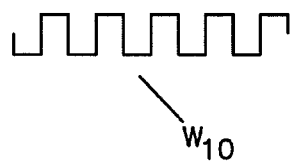
FIG. 12 is a schematic representation of a typical waveform according to aspects of the present disclosure.

A first blocking electrode configuration is shown in FIG. 11. This configuration creates a current path (see arrow 1 in FIG. 11) with current flowing between the anterior and posterior nerves AVN, PVN. The tip electrodes 212, 212a, which are located directly on the anterior and posterior vagal nerves AVN, PVN, respectively, are electrically active. The anodic ring electrodes 218, 218a are not energized.

A continuous waveform (e.g., the square waveform $W_{10}$ shown in FIG. 12) propagates along the current path (see arrow 1) extending across the esophagus E. Such an electrode configuration is generally monopolar (i.e., only one location on each nerve PVN, AVN is subject to the treatment) and could be accomplished with monopolar leads (i.e., leads without ring electrodes 218, 218a).

b. Blocking Electrode Configuration (2)

Figure 13:
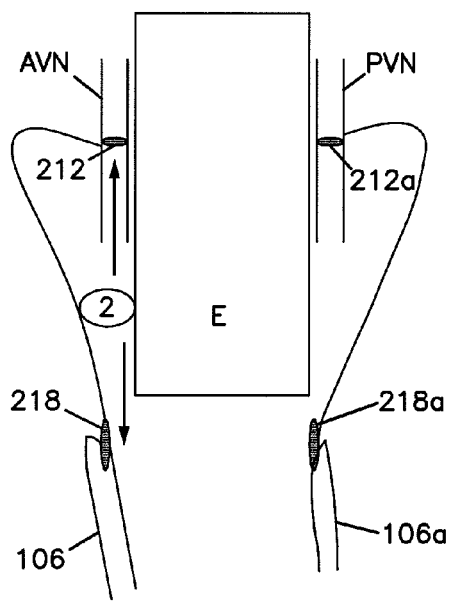
FIG. 13 is a schematic representation of a second electrode configuration according to aspects of the present disclosure.

FIG. 13 illustrates a second blocking electrode configuration in which each of the tip electrodes 212, 212a is associated with an anode electrode 218, 218a, respectively. Therapy signals are applied only to the anterior vagus nerve AVN between the distal electrode 212 and the anode electrode 218. Advantageously, current (see arrow 2 in FIG. 13) does not flow through the esophagus E, thereby decreasing the likelihood of the patient sensing the treatment (e.g., feeling discomfort or pain).

In general, the anode electrodes 218, 218a can be positioned on any anatomical structure. In a preferred embodiment, the anode electrodes 218, 218a are placed on structures in generally close proximity (e.g., within about five centimeters) of the tip electrodes 212, 212a. For example, the anode electrodes 218, 218a can be placed on the same vagal nerve PVN, AVN as the anode electrode's associated electrode 212, 212a.

Figure 14:
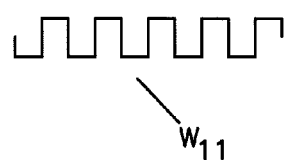
FIG. 14 is a schematic representation of a typical waveform according to aspects of the present disclosure.

In other embodiments, however, the anode electrodes 218, 218a can be placed on the stomach, the esophagus, or other anatomical structure in the general vicinity of the electrodes 212, 212a. In an embodiment, the anode electrodes 218, 218a can be placed on the stomach to permit monitoring of stomach contractions (e.g., by strain receptors associated with the anode electrodes 218, 218a). The arrangement of FIG. 13 results in a pacing waveform $W_{11}$ (FIG. 14).

c. Blocking Electrode Configuration (3)

Figure 15:
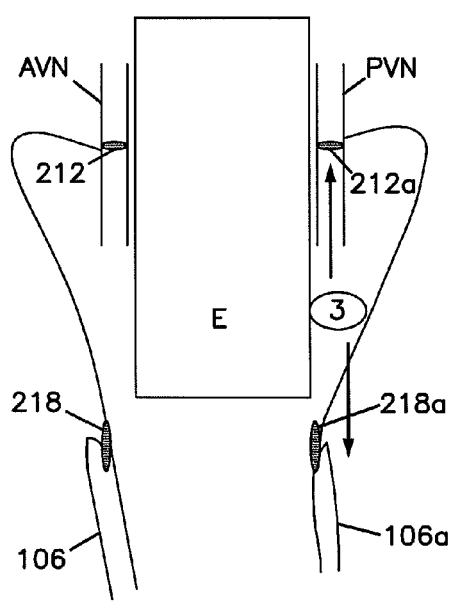
FIG. 15 is a schematic representation of a third electrode configuration according to aspects of the present disclosure.
Figure 16:
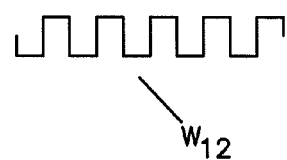
FIG. 16 is a schematic representation of a typical waveform according to aspects of the present disclosure.

FIG. 15 illustrates the same electrode configuration shown in FIG. 13, except the signals are applied only to the posterior vagus nerve PVN between the tip electrode 212a and the anode electrode 218a. The corresponding current path is shown by arrow 3 in FIG. 15. In an embodiment, the example signal waveform $W_{12}$ (see FIG. 16) propagating across the current path is the same as the waveform $W_{11}$ in FIG. 14. In other embodiments, however, any desired waveform can be utilized.

d. Blocking Electrode Configuration (4)

Figure 17:
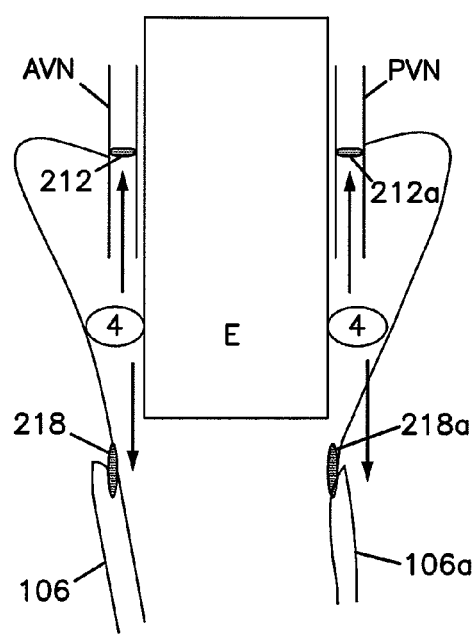
FIG. 17 is a schematic representation of a fourth electrode configuration according to aspects of the present disclosure.
Figure 18:
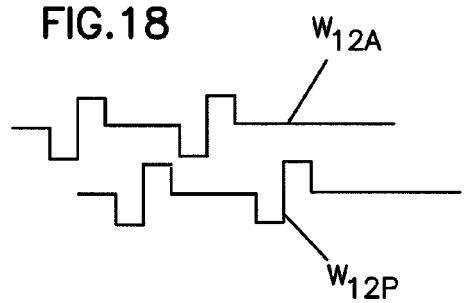
FIG. 18 is a schematic representation of a typical waveform according to aspects of the present disclosure.

The electrode configuration of FIG. 17 is generally the same as the electrode configurations of FIGS. 11, 13 and 15. In FIG. 17, however, an electrically active anode (e.g., ring electrode 218, 218a) and cathode (e.g., tip electrode 212, 212a) are associated with each nerve PVN, AVN to provide a dual channel system. Such an electrode arrangement routes current flow through both nerves PVN, AVN as indicated by arrows 4.

In an embodiment, a first electrode (e.g., the tip electrode 212, 212a) is placed directly on each of the nerve trunks and a second electrode (e.g., ring electrode 218, 218a) is located in proximity to the first electrode. Two waveforms (e.g., an anterior nerve waveform $W_{12A}$ and a posterior nerve waveform $W_{12P}$ shown in FIG. 18) are generated. In the example shown, the pulses of one of the waveforms occur during no-pulse periods of the other waveform. In such a configuration, a complete charging and rebalancing cycle can occur on one channel before the second channel is charged and rebalanced. Accordingly, only one channel is electrically paced at a time. Typically, the electrodes on the nerve are energized cathodically first.

3. Post-Operative Testing of Electrodes

After completing implantation, assembly, and positioning of the neuroregulator 104 and the electrode arrangement 108, a physician can determine the lead integrity by measuring the lead impedance and assessing whether the lead impedance is within an acceptable range. If the lead impedance is within range, the physician can connect an external computer 107 (e.g., a clinician computer) to the external charger 101 (see FIG. 1).

The clinician computer 107 can transmit treatment therapy settings and treatment data to the neuroregulator 104 via the external charger 101. The clinician computer 107 also can retrieve data from the external charger 101 or neuroregulator 104. For example, in one embodiment, the clinician computer 107 detects serial numbers of the external charger 101 and neuroregulator 104 automatically. After adjustment of blocking parameters and retrieval of data, the clinician computer 107 may be disconnected from the external charger 101.

After the patient has adequately recovered from the surgery (e.g., approximately fourteen days after the implantation surgery), the physician may program initial treatment parameters into the external charger 101. For example, the physician can couple the clinician computer 107 to the external charger 101 and follow menu commands on the computer 107 to upload select therapy programs to the external charger 101. In certain embodiments, the uploaded programs can then be transferred to the implanted neuroregulator 104.

Additionally, the physician can use the clinician computer 107 to select treatment start times for the patient. In an embodiment, treatment start times are selected based on the individual patient's anticipated waking and initial meal times. The start times can be set differently for each day of the week. Further details regarding scheduling treatment will be discussed herein with respect to FIG. 19.

4. System Software

The external charger 101 and the neuroregulator 104 contain software to permit use of the therapy system 100 in a variety of treatment schedules, operational modes, system monitoring and interfaces as will be described herein.

a. Treatment Schedule

To initiate the treatment regimen, the clinician downloads a treatment specification and a therapy schedule from an external computer 107 to the external charger 101. In general, the treatment specification indicates configuration values for the neuroregulator 104. For example, in the case of vagal nerve treatment for obesity, the treatment specification may define the amplitude, frequency, and pulse width for the electrical signals emitted by the implanted neuroregulator 104. In another embodiment, "ramp up" time (i.e., the time period during which the electrical signals builds up to a target amplitude) and "ramp down" time (i.e., the time period during which the signals decrease from the target amplitude to about zero) can be specified.

In general, the therapy schedule indicates an episode start time and an episode duration for at least one day of the week. An episode refers to the administration of therapy over a discrete period of time. Preferably, the clinician programs an episode start time and duration for each day of the week. In an embodiment, multiple episodes can be scheduled within a single day. Therapy also can be withheld for one or more days at the determination of the clinician.

During a therapy episode, the neuroregulator 104 completes one or more treatment cycles in which the neuroregulator 104 sequences between an "on" state and an "off" state. For the purposes of this disclosure, a treatment cycle includes a time period during which the neuroregulator 104 continuously emits treatment (i.e., the "on" state) and a time period during which the neuroregulator 104 does not emit treatment (i.e., the "off" state). Typically, each therapy episode includes multiple treatment cycles. The clinician can program the duration of each treatment cycle (e.g., via the clinician computer 107).

When configured in the "on" state, the neuroregulator 104 continuously applies treatment (e.g., emits an electrical signal). The neuroregulator 104 is cycled to an "off" state, in which no signal is emitted by the neuroregulator 104, at intermittent periods to mitigate the chances of triggering a compensatory mechanism by the body. For example, if a continuous signal is applied to a patient's nerve for a sufficient duration, the patient's digestive system eventually can learn to operate autonomously.

Figure 19:
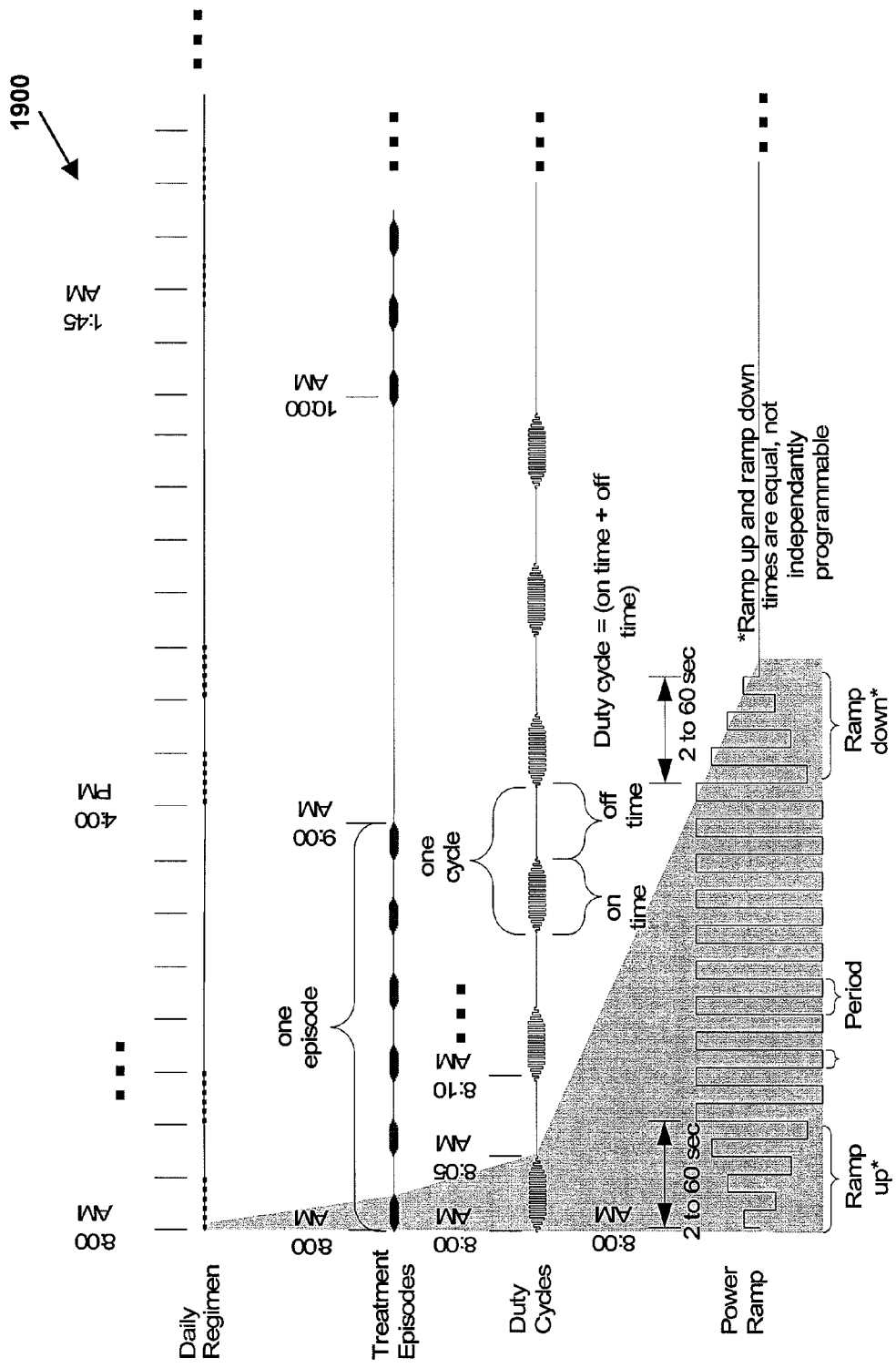
FIG. 19 is a graphical illustration of a treatment schedule according to aspects of the present disclosure.

An example daily treatment schedule 1900 is schematically shown in FIG. 19. The daily schedule 1900 includes a timeline indicating the times during the day when the treatment is scheduled to be applied to a patient. Duty cycle lines (dashed lines) extend along the time periods during which treatment is scheduled. For example, a first episode is scheduled between 8 AM and 9 AM. In certain embodiments, the treatment schedules 1900 address other details as well. For example, the daily schedule 1900 of FIG. 19 indicates details of the waveform (e.g., ramp-up/ramp-down characteristics) and details of the treatment cycles.

b. System Operational Modes

The therapy system 100 can be configured into two basic operational modes—a training mode and a treatment mode—as will be described herein. In an embodiment, the therapy system 100 also can be configured into a placebo mode for use in clinical trials.

i. Training Mode

The training mode is used post-operatively to train the patient on using the therapy system 100. In this mode, electrical signals are not delivered to the nerves for the purpose of creating blocking action potentials. In a preferred embodiment, the neuroregulator 104 does not generate any electrical signals. In some embodiments, the training therapy setting can be preset by the therapy system manufacturer and are unavailable to the treating physician.

The training mode allows the physician to familiarize the patient with the positioning of the external charger 101 relative to the implanted neuroregulator 104. The physician also instructs the patient in how to respond to the feedback parameters within the therapy system 100. Training also can cover information and menus which can be displayed on the external charger 101, for example: the status of the battery 182 of the external charger 101, the status of the battery 151 of the implanted neuroregulator 104, coil position, lead/tissue impedances, and error conditions.

The physician also can train the patient in how to interact with the external charger 101. In an embodiment, the patient interacts with the external charger 101 using the selection input button 174. For example, by successively pressing the button 174, the patient can select one of multiple device operations, such as: device reset, selective interrogation of battery status, and coil position status.

ii. Treatment Mode

The treatment mode is the normal operating mode of the neuroregulator 104 in which the neuroregulator 104 applies a blocking signal to the nerves using blocking therapy settings. In general, the therapy settings are specified by the physician based on the specific needs of the patient and timing of the patient's meals. In some embodiments, the neuroregulator 104 controls the therapy being provided according to therapy programs and schedules stored on the neuroregulator 104. In other embodiments, the neuroregulator 104 follows the instructions of the external charger 101 to deliver therapy.

iii. Placebo Mode

This mode may be used for patients randomized to a placebo treatment in a randomized, double-blind clinical trial. In this mode, the neuroregulator 104 does not apply therapy signals to the lead arrangement 108. Rather, in different embodiments, therapy signals can be supplied to a dummy resistor to drain the internal power source 151 (FIG. 3) of the neuroregulator 104.

The external charger 101 interacts with the patient and the physician as if therapy was being applied. For example, the patient and/or physician can view system status messages and a battery drain rate of the external charger 101 and neuroregulator 104. Because the external charger 101 functions as normal, the physician and the patient are blind to the fact that no significant therapy is being applied.

To give the patient the sensation that therapy is being applied, current pulses may be applied to the vagal nerve trunks during impedance measurements at the start of therapy. However, no therapy is delivered during the remainder of the blocking cycle. These sensations are felt by the patient and provide a misleading indication of activity. These sensations, therefore, help in maintaining the double blindness of the study.

c. Treatment Therapy Settings

The neuroregulator 104 is configured to provide therapy signals to the electrode arrangement 108. In general, the therapy signals can induce stimulation of the nerves, blocking of nerve impulses, or some combination of the two.

i. Blocking Treatment

During treatment, the neuroregulator 104 provides blocking signals to the nerves of a patient. Blocking signals include high frequency waveforms that inhibit the transmission of signals along the nerves. In general, the physician selects and sets therapy settings (e.g., waveform characteristics and treatment schedule) based on meal times and a patient's eating pattern. In an embodiment, the therapy system 100 can provide a choice of at least three unique blocking therapy settings which can be applied as part of a daily treatment schedule.

ii. Low Frequency Mode

The low frequency mode provides low frequency stimulating signals along the patient's nerves to create a brief, potentially observable, physiological response as an intra-operative screen. Such a physiologic response could be, for example, the twitching of a muscle or organ, such as the stomach.

This therapy setting may be used by the physician to confirm correct electrode placement. The system operates in this mode for short time periods and, typically, only when the patient is under physician care. This mode may be accessed through the programmer interface. In an embodiment, this mode can be enabled/disabled (e.g., by the manufacturer) through the programming interface.

iii. Temporary Test Therapy Setting Mode

The therapy system 100 has the ability to program special treatment/testing therapy settings to support "one-time" physiological evaluations. Special testing therapy parameters can be preset (e.g., by the manufacturer) to be made available for use by the physician.

d. System Monitoring

The therapy system 100 facilitates monitoring the operation of the therapy system 100 and its components. By monitoring the operation of the therapy system 100, faults and malfunctions can be caught early and dealt with before becoming problematic. The therapy system 100 can record the operation and/or the fault conditions for later analysis. The therapy system 100 also can notify the patient and/or physician of the system operating status and non-compliant conditions. For example, an error message can be displayed on screen 172 (see FIG. 5) of the external charger 101 or on a display screen (not shown) of the external computing device 107 (see FIG. 1).

Embodiments of the therapy system 100 can confirm proper functioning of and communication between the components of the therapy system 100. For example, the therapy system 100 can monitor the link strength between the external charger 101 and the neuroregulator 104. In an embodiment, immediate feedback indicating the link strength can be provided to the patient (e.g., through the display 172 of the external charger 101) and/or to the physician (e.g., through the external computing device 107).

The therapy system 100 also can determine one or both of the coils 102, 105 are broken, shorted, or disconnected. In an embodiment, the therapy system 100 determines whether the coils 102, 105 are operational by measuring the impedance between the coils and determining whether the measured impedance falls within an acceptable range.

The therapy system 100 also can measure the impedance between the electrodes 212, 212a of the lead arrangement 108 and determine whether the impedance is out of range (e.g., due to inadequate electrode-nerve contact, or shorted electrodes). Details regarding the measurement of lead impedance are discussed later herein. Impedance measurements also can be used to verify proper lead placement, verify nerve capture, and monitor stomach contraction during the implant procedure.

The therapy system 100 also can communicate other types of system errors, component failures, and software malfunctions to the patient and/or physician. For example, the therapy system 100 can monitor the battery status (e.g., low battery, no charge, battery disconnected, etc.) of the neuroregulator 104 and/or the external charger 101 and warn the patient and/or physician when the battery should be recharged and/or replaced.

The therapy system 100 can indicate an inability to deliver a signal having the specified current (e.g., due to the impedance being out of range or due to internal component failure) to the lead arrangement 108 during treatment delivery. The therapy system 100 also can indicate whether the external charger 101 and/or the neuroregulator 104 have sufficient power to transmit and/or receive signals (e.g., based on antenna alignment, battery power, etc.).

i. Lead Impedance Measurement

Embodiments of the therapy system 100 have the ability to independently measure and record lead impedance values. Lead impedance values outside a predefined range may indicate problems or malfunctions within the therapy system 100. High impedance, for example, could mean that the electrodes 212, 212a are not properly coupled to the nerves of the patient. Low impedance could mean inappropriate shorting of the electrodes 212, 212a.

These embodiments of the therapy system 100 allow the physician to measure lead impedance on-demand. The therapy system 100 also can enables the physician to periodically measure impedance (e.g., during the Training Mode) without initiating a blocking therapy setting. Generally, impedance is measured and stored separately for each channel of each electrode configuration. These measurements may be used to establish a nominal impedance value for each patient by calculating a moving average. The nominal impedance and impedance tolerance range can be used for system non-compliance monitoring, as will be described below.

e. External Computer Interface

Programmer software, with which the physician can program treatment configurations and schedules, resides on and is compatible with an external computing device 107 (FIG. 1) that communicates with the external charger 101. In general, application software for the computing device 107 is capable of generating treatment programs stored in a commonly accepted data file format upon demand.

The programming interface of the computing device 107 is designed to enable the physician to interact with the components of the therapy system 100. For example, the programming interface can enable the physician to modify the operational modes (e.g., training mode, treatment mode) of the external charger 101. The programming interface also can facilitate downloading treatment parameters to the external charger 101. The programming interface enables the physician to alter the treatment parameters of the neuroregulator 104, and to schedule treatment episodes via the external charger 101.

The programming interface also enables the physician to conduct intra-operative testing amongst the components of the therapy system 100. For example, the physician can initiate a lead impedance test via the programming interface. The physician also can program temporary treatment settings for special physiologic testing. The programming interface also can facilitate conducting diagnostic stimulation at follow-up visits between the patient and the physician.

The programming interface of the computing device 107 also enables the physician to access patient data (e.g., treatments delivered and noted physiological effects of the treatment). For example, the programming interface can enable the physician to access and analyze patient data recorded by the therapy system 100 (e.g., stored in the memory 152 of the neuroregulator 104 and/or the memory 181 of the external charger 101). The physician also can upload the patient data to the external computing device 107 for storage and analysis.

The programming interface also can enable the physician to view system operation information such as non-compliant conditions, system faults, and other operational information (e.g., lead impedance) of the therapy system 100. This operational data also can be uploaded to the external computing device 107 for storage and analysis.

i. Programming Access Level

In certain embodiments, the programming interface defines at least two levels of access, one for the physician and one for the system manufacturer. The programming interface can provide different types of information to a requestor depending on what level of access the requestor has. For example, the programming interface may enable the system manufacturer to program system settings (e.g., default values for treatment parameters, acceptable ranges for treatment parameters and/or system settings, system tolerances, etc.) that cannot be adjusted by the physician.

In an embodiment, a user with a high level of access can select, for each system setting, the level of access required before the programming interface will enable a user to modify the system setting. For example, the system manufacturer may wish to prevent treating physicians from modifying default treatment settings. It will be appreciated that generating software implementing the above-described features of the programming interface is within the skill of one of ordinary skill in the art having the benefits of the teachings of the present application.

5. Charge Balancing

Nerves may be damaged when exposed to direct current (e.g., net current from electrical stimulation) over extended periods of time. Such damage may result from very small net currents acting over a long time, e.g. microamperes of current over minutes. For example, direct current can be caused by a voltage buildup at the electrodes 212, 212a (FIG. 1) due to inherent differences in electrode component values.

Charge-balancing advantageously mitigates (and may eliminate) damage to the nerve due to charge build-up during treatment. However, conventional processes for achieving a current/charge balance to within (for example) 1 µA in a current of about 6 mA place inordinate requirements on the implantable device of providing consistent power at a consistent frequency. Below are descriptions of two processes for balancing charge, a timing process and a shorting process, that do not require such inordinate consistency.

a. Timing Correction

Figure 20:
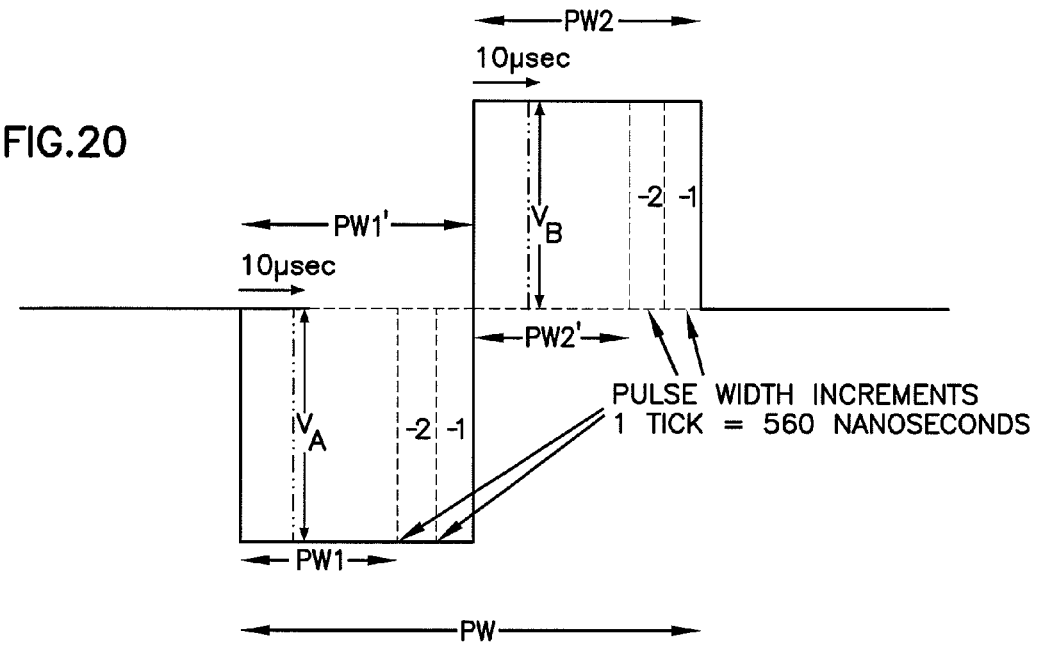
FIG. 20 is a schematic representation of a signal pulse illustrating charge balancing according to aspects of the present disclosure.

Referring to FIGS. 20-24, charge or current on the patient's nerves can be balanced by applying a correction to a pulse-width PW of a treatment signal pulse 2000 over a number of cycles (see FIG. 20). A cycle refers to a single iteration of the pulse. The correction includes adding or subtracting a "timer tick" to the pulse-width PW of at least one phase of the treatment signal pulse 2000 to increase or decrease the pulse-width for a period of time. In an embodiment, an example timer tick can equate to the minimum resolution of the applied clock frequency (e.g., about 560 nanoseconds).

Typically, the treatment signal pulse 2000 is a bi-phasic (e.g., having a negative phase and a positive phase) pulse signal having a pulse-width PW. In general, the negative charge provided by the first phase of the signal pulse 2000 is balanced by the positive charge provided by the second phase of the signal pulse 2000. One or more timer ticks can be added to one or both phases of the pulse 2000 to correct a charge imbalance.

In the example shown in FIG. 20, the first phase of the signal pulse 2000 has a first pulse-width PW1 and the second phase of the signal pulse 2000 has a second pulse-width PW2. One or more timer ticks can be added to the pulse-width PW1, PW2 of one or both phases of the signal pulse 2000. For example, the pulse-width PW1 of the first phase can be increased by two timer ticks to a pulse-width of PW1'. Alternatively, the pulse-width PW2 of the second phase can be decreased by two timer tick to a pulse-width of PW2'.

To determine the number of timer ticks to add or subtract from each pulse-width, the neuroregulator 104 periodically can measure the voltage of the signal applied to each lead electrode 212, 212a of lead arrangement 108. The combination of charge buildup sensing and pulse width control creates a feedback loop to minimize the resulting voltage offset. Advantageously, this sense and control process is effective in the presence of physiologic variations, circuit tolerances, differences in electrode size, and temperature changes.

For example, as shown in FIGS. 3A and 3B, the electrodes of each lead (e.g., the tip electrodes 212, 212a in contact with the anterior and posterior vagal nerves AVN, PVN, respectively) are coupled to the CPU 154 of the neuroregulator 104 via a capacitive divider 162. The CPU 154 provides timed instructions to the output module 161 for controlling the voltage measurements $V_A$, $V_B$ of the signals applied by the electrodes 212, 212a (FIG. 1).

Between pulses, the microprocessor CPU 154 can zero the capacitive divider 162, release the capacitive divider 162 at a predetermined time relative to the signal cycle, and measure the voltages $V_A$, $V_B$ of the electrodes 212, 212a. For example, the CPU 154 can zero the capacitive divider 162, release the capacitive divider 162 approximately ten microseconds into a negative phase of the pulse, and measure the voltages $V_A$, $V_B$ (see FIG. 20). The CPU 154 can subsequently measure the voltages $V_A$, $V_B$ at approximately 10 microseconds into a positive phase of the pulse. If the voltage measurement $V_A$ of the electrode 212 is greater than the voltage measurement $V_B$ of the second electrode 212a, then the CPU 154 delivers instructions to decrease the pulse width (e.g., by about 560 nanoseconds) of the negative phase of the pulse of the next/subsequent cycle.

The above process may be repeated at a sampling frequency (e.g., typically about 40 Hz). Gradually, the number of pulse width corrective increments ("timer ticks") applied to the signal can be adjusted. For example, the pulse width PW1 of the positive phase of the pulse can be increased or decreased every sample period until the voltage measurement $V_A$ of the first electrode 212 is less than the voltage measurement $V_B$ of the second electrode 212a. In such a case, the pulse width PW2 of the negative pulse then can be increased to achieve balance. When the maximum pulse width PW2 of the negative phase of the pulse is reached, then the pulse width PW1 of the positive phase of the biphasic pulse may be decreased to maintain balance. In a preferred embodiment, the corrective increment is applied to a series of signals until the net offset current is well below a target current (e.g., about 1 µA).

In an embodiment, the amplitudes of the positive and negative phases of the pulse are compared very early in the cycle, and a relatively large correction is initially applied to the pulse width of the signal. Subsequently, the balancing correction is refined by changing the pulse width by only the one or two ticks as described above.

Advantageously, the charge-balancing goal can be achieved over a number of these cycles using the above described processes without requiring a high clock frequency. Because the charge buildup tends to be a slow process, correcting the charge buildup can be done less frequently than delivering therapy signals. For example, in an embodiment, therapy signals can be delivered at about 5 kHz and correction pulses can be delivered at about 40 Hertz.

Figure 21:
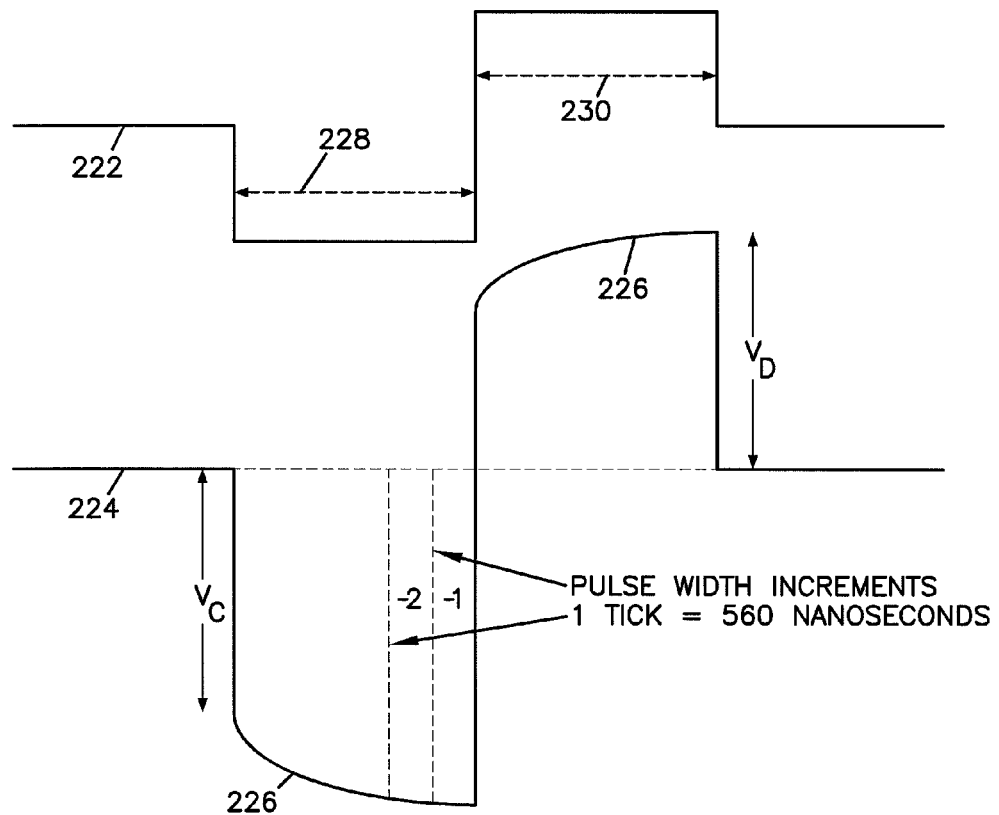
FIG. 21 is a schematic representation of an alternative means of charge balancing according to aspects of the present disclosure.

FIG. 21 illustrates an example application of charge balancing through timing corrections. FIG. 21 illustrates a blocking waveform 222 (e.g., a biphasic, symmetric current waveform), which results in a voltage waveform 224 at the electrode-tissue interface. The voltage waveform 224 includes an exponential voltage component 226 which reflects the fact that the electrode-tissue interface has capacitive elements, resulting in charging and discharging of this capacitance.

In one cycle of the current waveform 222, the charge applied to the electrode-tissue interface is balanced when the voltages $V_C$ and $V_D$ are equal. Accordingly, in such a case, the net potential of the electrode-tissue interface is zero. As described above, however, there are a number of reasons why, in practice, voltages $V_C$ and $V_D$ may not be equal, resulting in a charge imbalance.

Typically, in practical operation, the voltage values of $V_C$ and $V_D$ are measured periodically (e.g., about every 25 milliseconds). If the voltage $V_C$ is greater than the voltage $V_D$, then the pulse width 228 of the first phase of the current waveform 222 is reduced by one "timer tick," and applied for about 1 millisecond. At the end of subsequent measurement periods (e.g., about every 25 milliseconds), the values of voltages $V_C$ and $V_D$ are measured again. When the voltage $V_C$ is greater than the voltage $V_D$, the pulse width 228 of the first phase is reduced by an additional timer tick. The current waveform 222 having the phase with the reduced pulse-width 228 is applied for an additional 1 millisecond.

When the value of the voltage $V_C$ is eventually less than the value of the voltage $V_D$, then the pulse width 228 of the first phase can be increased by one timer tick for 1 millisecond for each measurement period. In this situation, it may be that the maximum pulse width (as determined by the applied frequency of the therapy) 228, is reached while the voltage $V_C$ is still less than the voltage $V_D$. If this occurs, then the pulse width 230 of the second phase of the current pulse 222 is decreased one timer tick at a time, as described above, until equilibrium is established (i.e., $V_C = V_D$).

Additionally, in the methods represented by FIGS. 20 and 21, the microprocessor CPU 154 can short out the electrodes 212, 212a at the beginning, midpoint and/or end of the biphasic, square-wave, current pulse, as described in more detail herein. Over a series of such sampling cycles, it has been demonstrated that the net offset current is well below the design goal of 1 µA.

During a feedback cycle, software stored in the microprocessor CPU 154 can initiate a therapy shut down if the sensed voltage offset exceeds safe values. This is an advantageous feature in actual use, where electrode configurations and other parameters could vary.

By using a combination of both hardware (i.e., electrode shorting) and closed-loop software techniques, the average charge imbalance may be lower than with either method individually.

At the end of therapy delivery, it is useful to have the hardware briefly drain any residual charge. Subsequently, the circuitry may be made safe until the next therapy delivery and the software loop turned off.

b. Shorting Correction

Some processing for achieving charge balance have involved the use of biphasic pulses in which, for example, the negative charge provided by the first part of the waveform is balanced by the positive charge provided by the second part of the waveform. Further details describing the use of electrode shorting to achieve charge balancing can be found in U.S. Pat. No. 4,498,478 to Bourgeois, issued Feb. 12, 1985; U.S. Pat. No. 4,592,359 to Galbraith, issued Jun. 3, 1986; and U.S. Pat. No. 5,755,747 to Daly et al, issued May 26, 1998, the disclosures of which are hereby incorporated by reference herein.

Figure 22:
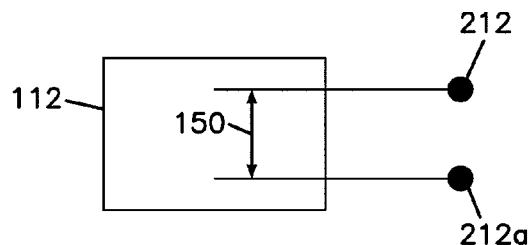
FIG. 22 is a schematic illustration of a charge balancing system shown in a shorting state according to aspects of the present disclosure.
Figure 23:
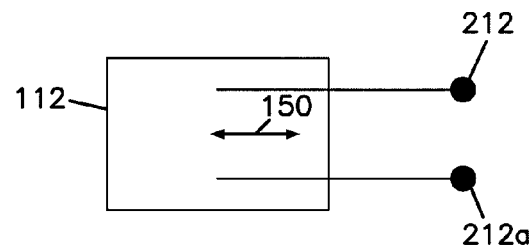
FIG. 23 is the view of FIG. 22 in a non-shorting state according to aspects of the present disclosure.
Figure 24:
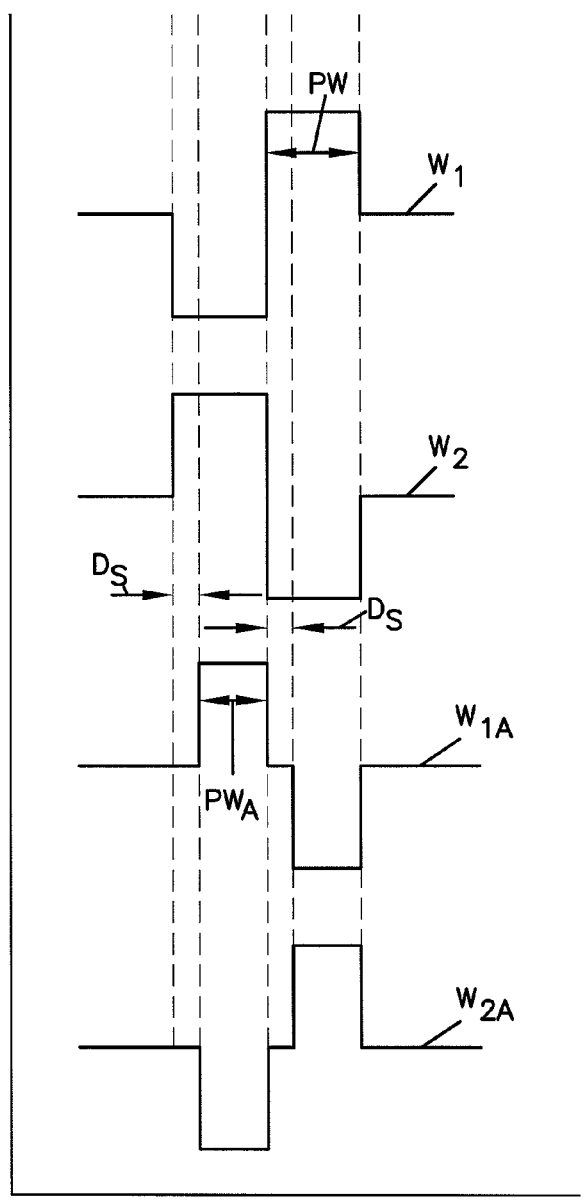
FIG. 24 is a graphical illustration comparing waveforms in shorting and non-shorting states according to aspects of the present disclosure.

FIGS. 22-24 illustrate a preferred charge balancing process. FIGS. 22 and 23 schematically illustrate an implanted circuit 112 of a neuroregulator 104 connected to nerve electrodes 212, 212a. The circuit 112 has components schematically illustrated as a switch 150 for selectively creating an electrical short between the electrodes 212, 212a. In FIG. 22, the switch 150 is arranged in a short state to create an electrical short between electrodes 212, 212a. In FIG. 23, the switch 150 is arranged in a non-short state with no short being created between the electrodes 212, 212a.

FIG. 24 schematically illustrates signal waveforms $W_1$, $W_2$, $W_{1A}$, $W_{2A}$ produced at the electrodes 212, 212a under various conditions of operation of the switch 150. The waveforms $W_1$ and $W_2$ show the signals produced at electrodes 212, 212a, respectively, when the switch 150 is arranged in the non-short state. Each waveform $W_1$ and $W_2$ has a negative pulse and a positive pulse of equal pulse width PW. The waveforms $W_1$, $W_2$ are out of phase so that the negative pulses of the waveform $W_1$ occur during the positive pulses of the waveform $W_2$.

It will be appreciated, these waveforms are illustrative only. Any other waveform (e.g., the time offset waveform $W_{12A}$ of FIG. 18 could be used). In addition, while the short is shown between electrodes 212, 212a, the short alternatively or additionally could be created between cathode and anode pairs 212, 218 and 212a, 218a, previously described.

In the example shown, the switch 150 is operated to create a short between electrodes 212, 212a at the start of each pulse and for a duration $D_S$. The waveforms at electrodes 212, 212a resulting from such shorting are shown in FIG. 24 as $W_{1A}$, $W_{2A}$. As a result of the short, any charge build-up at an electrode (e.g., electrode 212) is distributed to the oppositely charged electrode (e.g., electrode 212a). The pulse width PW of each pulse is reduced to a pulse width $PW_A$. Advantageously, repeating this process throughout the therapy maintains any net charge build-up below tolerable levels.

The example given shows the short state occurring at the beginning of each signal pulse. This is illustrative only. The short state can occur at the beginning, end or any intermediate time of a signal pulse. Furthermore, the short state need not be applied to every pulse, but rather can occur intermittently throughout the pulse cycles or even during time delays between pulses. When applied during a pulse cycle, the duration Ds of the short is preferable not greater than about 10% of the pulse width PW. For example, the duration Ds can range from about 10 μs to about 20 μs.

6. Therapy Calibration and Safety Limits

The design of the neuroregulator 104 (FIG. 3) includes a capacitive divider 162 and an output module 161 to measure the voltage present at the lead arrangement 108 (e.g., the tip electrodes 212, 212a and/or ring electrodes 218 and 218a of both anterior and posterior leads 106, 106a). The output module 161 can measure the current flow through the electrodes arranged in any of the four electrode configurations (see FIGS. 11, 13, 15, and 17). A programmable current source (not shown) can enable a physician to select how current is delivered through the electrodes 212, 212a, 218, and 218a to the nerve.

Before therapy is delivered, the physician can calibrate the neuroregulator 104 to ensure the desired current can be delivered to the nerves. For example, this calibration can be accomplished by connecting the programmable current source from a power source to ground and adjusting the current to the desired level. Current does not flow through the leads 106 during this calibration procedure. If the desired current cannot be delivered, or if the DC voltage offset is greater than a programmed limit, then the therapy can be terminated (e.g., such conditions trigger a flag or error alert).

Advantageously, calibrating the therapy system 100 significantly reduces the effect of component tolerance, drift, and aging on the amount of current delivered. Temperature effects are not likely to be significant since the neuroregulator 104 is at body temperature when implanted. In addition, the capacitive divider 162 can be calibrated before therapy is delivered. Advantageously, calibrating the divider 162 can enhance the accuracy of the safety checks from a 20% worst case value to approximately 2%.

During therapy, the current between the active electrodes is measured during each signal pulse to ensure that the delivered current is within the programmed tolerance (e.g., +/−about 5%).

Additionally, in order to determine the state of charge balance, the therapy system 100 can determine a peak-to-peak voltage quantity for each signal pulse. The peak-to-peak voltage quantity is divided by two and compared to the peak voltage measurement of each phase of the waveform. If the deviation exceeds a predetermined value, the therapy can be shut down.

The normal shutdown of the output module 161 shorts the electrodes together and connects them to ground through one of the current sources. Normally, this is a desirable and safe condition. However, certain failures could cause current to flow after shutdown, resulting in damage to the nerve. To eliminate this problem, an additional check can be made after normal shutdown has been completed. If current flow is detected, the leads are disconnected from each other (allowed to float) and the current sources are programmed to zero current.

7. Auto-Increment Therapy Delivery

For blocking therapy to be effective, energy delivery may need to be increased beyond the level that a patient perceives as acceptable at the initiation of therapy. The power of the therapy signals can be increased in small increments to enable the patient to acclimate to the more powerful therapy signals.

For example, the current of the therapy signal can be increased in steps of about 1 mA at weekly follow-up visits. Over time, patients may willingly accept multiple increments of 1 mA/week through periodic follow-up visits and programming sessions. For example, an initial setting of 3 mA may rise to at least 6 mA as a result of such follow-up sessions.

In certain embodiments of the therapy system 100, energy (i.e., power) delivery can be incrementally increased or decreased automatically over a predetermined period of time.

Advantageously, this automatic incremental increase can mitigate the need for frequent doctor office visits. This flexibility is especially convenient for patients who are located remote from the implanting bariatric center.

In an embodiment, the therapy system 100 automatically increases the current of the therapy signal by, for example, 0.25 mA every other day, cumulatively achieving the 1 mA/week incremental increase. In another embodiment, the therapy system 100 increases the current by about 0.125 mA per day. Initial studies have demonstrated such increment levels as acceptable.

The patient can retain the ability to turn therapy off at any time and return to the physician for re-evaluation. Alternatively, the patient can revert to previously acceptable therapy delivery levels (e.g., the therapy level of the previous day). For example, the patient can interact with the external charger 101 to issue such an instruction.

The physician can choose whether to activate the auto-increment therapy capability. The physician also can specify the date and/or time of therapy initiation and therapy parameters (e.g., including the starting and ending therapy parameters). The physician also may specify safety limits or tolerances for the therapy parameters. Additionally, the physician can specify the rate at which the therapy parameters are incremented over various time periods (e.g., about 0.5 mA/day for the first 7 days, then 0.125 mA/day over the following 24 days).

8. Predetermined Programs

One or more therapy programs can be stored in the memory of the external computer 107. The therapy programs include predetermined parameters and therapy delivery schedules. For example, each therapy program can specify an output voltage, a frequency, a pulse width, ramp-up rates, ramp-down rates, and an on-off cycle period. In an embodiment, the ramp-up rates and ramp-down rates can be individually and separately programmed.

In use, the physician may select any one of these therapy programs and transmit the selected therapy program to the implanted neuroregulator 104 (e.g., via the external charger 101) for storage in the memory of the neuroregulator 104. The stored therapy program then can control the parameters of the therapy signal delivered to the patient via the neuroregulator 104.

Typically, the parameter settings of the predetermined programs are set at the factory, prior to shipment. However, each of these parameters can be adjusted over a certain range, by the physician, using the computer 100 to produce selectable, customized, predetermined therapy programs. Using these selectable, customized therapy programs, the physician can manage the patient's care in an appropriate manner.

For example, when patients require more varied therapies, the neuroregulator 104 can store a therapy program including one or more combinations of multiple therapy modes sequenced throughout the day.

For example, referring to electrode configuration shown in FIG. 10, a single therapy program can include instructions to apply a blocking signal between electrode tips 212 (anterior vagal nerve) and 212a (posterior vagal nerve) from 8 a.m. to noon at 6 mA and 5 kHz; alternating between applying a blocking signal to posterior tip 212a to ring 218a and applying a blocking signal to anterior tip 212 to ring 218 from noon to 2 p.m. at 3 mA and 2.5 kHz; and applying a blocking signal from electrode tip 212 to electrode tip 212a from 2 p.m. from 2 p.m. to midnight at 6 mA and 5 kHz.

9. Operation Logs

In general, the neuroregulator 104 can have a time base to facilitate the delivery of therapy according to the treatment schedule. To determine this time base, the neuroregulator 104 can maintain one or more operating logs indicating the operations of the therapy system 100.

For example, the neuroregulator 104 maintains a time-and-date-stamped delivery log of the actual delivery of therapy. For example, the delivery log can include the time and date of initiation of each therapy episode, the time and date of completion of the therapy episode, the therapy parameters associated with the therapy episode. Both scheduled therapy and automatically-initiated therapy can be logged. The delivery log also can include a parameter to indicate whether the therapy episode was scheduled or automatically initiated.

Additionally, the neuroregulator 104 can maintain a time-and-date-stamped error log of all conditions that interfered with the delivery of therapy. For example, the error log can record all impedances measured, temperatures measured by the on-board temperature sensor, each instance in which the battery was charged by the external charger 101, each instance in which the battery reached its low-charge threshold, and each instance in which the battery reached its depleted threshold.

The delivery log and the error log are readable by the external computer 107 (e.g., a clinician programmer). In an embodiment, the delivery log and the error log each can accommodate up to about 3 months of data.

10. Detection of Food Passage Through the Esophagus

Neural blocking therapy can affect the rate at which the stomach empties and the level of intestinal motility. When applying neural blocking therapy for obesity control, it is desirable to determine the approximate times at which the patient ingests food (i.e., mealtimes) and the approximate quantity of food being consumed at each meal. Advantageously, with this information, the duty cycle of the therapy system 100 can be synchronized with the mealtimes. Additionally, the nature of the therapy can be adjusted in accordance with the quantity of food being consumed. For example, food detection is described in U.S. Pat. No. 5,263,480 to Wernicke et al, issued Nov. 23, 1993, the disclosure of which is hereby incorporated herein by reference.

In certain embodiments of the therapy system 100, the anterior and posterior vagal nerve electrodes 212, 212a can be positioned on the esophagus E adjacent to the junction between the esophagus E and the stomach. An impedance measurement between the anterior and posterior vagal nerve electrodes 212, 212a provides a measure of the presence of food in the esophagus E between the electrodes 212, 212a (e.g., see FIG. 11). The time integration of this impedance value provides a measure of the quantity of food consumed.

The impedance value between the electrodes 212, 212a can be measured by passing a low amplitude, sinusoidal signal (e.g., having a frequency of about 500-1000 Hz) between the electrodes 212, 212a. In an alternative embodiment, the impedance can be measured by passing the signal between the ring electrodes 218, 218a. In other embodiments, the dual bipolar lead/electrode configuration can operate as a quadripolar array.

In a quadripolar electrode array, two pairs of electrodes are typically secured in generally the same plane and normal to the length of the esophagus E. In such a configuration, a small signal applied across one pair of the electrodes (e.g., tip electrode 212, ring electrode 218) can be detected across the other pair (e.g., tip electrode 212a, ring electrode 218a). In general, changes in relative amplitude of the detected signal are proportional to changes in resistance of the signal path.

The impedance of the signal changes when food progresses down the esophagus E. This impedance change causes the amplitude of the detected signal to change, thereby providing an indication of the fact that food has passed, and giving an indication of the quantity of food. While a bipolar electrode pair may be used for both signal application and sensing across the esophagus E, it has the disadvantage of some interference as a result of polarization potentials.

More generally, this technology can be used to detect changes in the nature of the fluid within a vessel or lumen of the body. Such technology can be utilized in multiple applications. For example, this impedance measurement technology can be used to detect the presence of liquid/food in the distal esophagus to ascertain the presence of esophageal reflux. In another embodiment, this impedance measurement technology can be used in diagnosing eating abnormalities, such as bulimia.

In one embodiment, the time history of the transesophageal impedance measurement is recorded in the memory of the implanted module (e.g., in an operating log), for later telemetry to the external module, for review and analysis by the physician. With this information, the physician can preferentially choose the operating parameters of the system to best suit the eating habits of an individual patient.

In an alternative embodiment, the output of the transesophageal impedance measurement becomes a control input into CPU 154 of circuit 112 in neuroregulator 104 (FIG. 3). The therapy signal output of the neuroregulator 104 can be timed automatically to correspond to the timing and quantity of food consumed via a suitable algorithm.

11. Activity Monitoring System

The weight reduction resulting from the application of therapy described in this patent application is expected to produce an increased feeling of well-being in the patient, and possibly an increase in the amount of activity in which the patient is comfortable becoming involved.

In certain embodiments, the therapy system 100 monitors the activity of the patient. Generally, the therapy system 100 records the change in activity over the course of treatment. The therapy is applied to accomplish a goal (e.g., obesity reduction), and the activity level as a consequence of achieving the goal (e.g., weight loss) is then measured.

In an embodiment, this change in activity then can be mapped to the affects of the treatment. This mapping of the change in activity to the results of treatment can be personally advantageous to patients as well as advantageous to the medical community. For example, knowledge of the likely change, both in weight and in activity level, could be useful information for patients who are contemplating the implant and associated therapy.

In addition, such mapping would advantageously provide documented evidence of the positive effect of the weight control system to reimbursement groups. Additionally, from a medical/scientific perspective, it is known that weight loss is generally related to caloric intake, activity level, and metabolic rate. Increased quantification in the area of activity level would aid in developing a robust relationship among these factors.

There are a variety of methods which can be used for measuring activity level. Some of these models have been used as the basis for determining the preferred rate of implantable pacemakers and defibrillators. For example, a sensor of movement or acceleration (e.g., a gyroscope-based sensor), can provide an instantaneous measurement of activity level. Suitable hardware, software, and/or algorithm systems can then derive from these measurements the activity level averaged over a period of time (e.g., a 24 hr period).

An accelerometer also can be used to track patient activity. Other examples of activity sensing options include tracking the respiratory rate of the patient, by monitoring bio-impedance measurements (e.g., intrathoracic impedance), measuring a minute volume of, e.g., a compendium of respiratory rate and tidal volume, and monitoring blood pH, blood oxygen level, and blood pressure. In each case, the instantaneous value of the measurement can be integrated over a suitable time period.

With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto.

What is claimed is:

1. A system for applying therapy to an internal anatomical feature of a patient comprising:
   at least one electrode configured to be implanted within a body of the patient beneath a skin layer and placed at the anatomical feature, the electrode also configured to apply therapy to the anatomical feature upon application of a signal to the electrode;
   an implantable component for placement in the body of the patient beneath the skin layer, the implantable component being configured to generate the signal and to transmit the signal to the electrode, the implantable component being coupled to an implanted antenna;
   an external component including an external antenna configured to be placed above the skin layer and adapted to communicate with the implanted antenna across the skin layer through radiofrequency communication, the external component having at least three operating modes selected from a group consisting of an operating room mode, a programming mode, a therapy delivery mode, a charging mode, and a diagnostic mode, each operating mode being associated with a different set of operations available for selection by a user.

2. The system of claim 1, wherein the external component includes a first user interface configured to receive user input including a selection of one of the operating modes.

3. The system of claim 1, wherein the external component defines at least a first port and the external antenna is coupled to the external component at the first port.

4. The system of claim 3, further comprising an external power source configured to be received at the first port, wherein the external component receives power from the external power source when the external power source is received at the first port, and wherein the external power source cannot be received at the first port when the external antenna is received at the first port.

5. The system of claim 4, wherein the external component is configured to transmit at least some of the power received from the external power source to the implantable component.

6. The system of claim 1, further comprising an external programmer configured to communicatively couple to the external component at a second port, the external programmer being configured to provide therapy instructions to the external component, wherein the external component is configured to send the therapy instructions to the implantable component via the external antenna and the implanted antenna.

7. The system of claim 6, wherein the external programmer includes a personal computer.

8. The system of claim 6, wherein the external programmer is configured to obtain patient data stored on the external component, the external component having received the patient data from the implantable component.

9. The system of claim 6, wherein the external component is adapted to be configured into a programming mode when the external programmer is coupled to the external component at the second port, wherein the external component does not provide power to the implantable component when configured in the programming mode.

10. A therapy system for applying therapy to an internal anatomical feature of a patient, the system comprising:
an implantable component configured to be implanted within the body of the patient beneath a skin layer, the implantable component configured to deliver therapy to the internal anatomical feature;
an implanted antenna implanted within the body of the patient and coupled to the implantable component;
a first external antenna configured to communicate with the implanted antenna across the skin layer;
a second external antenna configured to communicate with the implanted antenna across the skin layer; and
an external component defining a first port configured to receive either the first external antenna or the second external antenna, the external component being configured to communicate with the implantable component by sending communication signals between the received external antenna and the implanted antenna, the external component being adapted to be configured into at least two different operating modes, each operating mode being associated with different operation instructions for the implantable component, wherein a first of the operating modes is associated with the first external antenna and a second of the operating modes is associated with the second external antenna such that plugging one of the external antennas into the first port automatically configures the external component into the associated operating mode.

11. The system of claim 10, further comprising at least one electrode configured to be implanted within a body of the patient and arranged adjacent the anatomical feature, the electrode being configured to apply therapy to the anatomical feature upon receipt of an electrical signal at the electrode, the electrical signal having been generated at the implantable component.

12. The system of claim 10, wherein the first external antenna has a cable extending along a first length and the second external antenna has a cable extending along a second length that is longer than the first length.

13. The system of claim 12, wherein the second length of the cable of the second external antenna is sufficient to enable the external component to be located outside a sterile area in an operating room when the second external antenna is received at the first port of the external component and aligned with the implanted antenna.

14. The system of claim 10, wherein the second external antenna is associated with an operating room mode.

15. The system of claim 14, wherein the operating room mode enables a physician to conduct a plurality of system and patient response tests.

16. The system of claim 10, wherein the second external antenna includes a resistor, which can be recognized by the external component when the second antenna is received at the first port.

* * * * *